US011568957B2

(12) United States Patent
Reid et al.

(10) Patent No.: US 11,568,957 B2
(45) Date of Patent: *Jan. 31, 2023

(54) METHODS AND SYSTEMS FOR COPY NUMBER VARIANT DETECTION

(71) Applicant: Regeneron Pharmaceuticals Inc., Tarrytown, NY (US)

(72) Inventors: Jeffrey Reid, Stamford, CT (US); Lukas Habegger, Stamford, CT (US); Jonathan Packer, Hartsdale, NY (US); Evan Maxwell, Danbury, CT (US)

(73) Assignee: Regeneron Pharmaceuticals Inc., Tarrytown, NY (US)

( * ) Notice: Subject to any disclaimer, the term of this patent is extended or adjusted under 35 U.S.C. 154(b) by 572 days.

This patent is subject to a terminal disclaimer.

(21) Appl. No.: 16/460,420

(22) Filed: Jul. 2, 2019

(65) Prior Publication Data

US 2020/0035326 A1 Jan. 30, 2020

Related U.S. Application Data

(63) Continuation of application No. 14/714,949, filed on May 18, 2015, now Pat. No. 10,395,759.

(51) Int. Cl.
| | | |
|---|---|---|
| *G01N 33/48* | (2006.01) | |
| *G16B 20/10* | (2019.01) | |
| *G16B 30/00* | (2019.01) | |
| *G16B 40/00* | (2019.01) | |
| *G16B 20/00* | (2019.01) | |
| *G16B 20/20* | (2019.01) | |
| *G16B 40/30* | (2019.01) | |
| *C12Q 1/6869* | (2018.01) | |

(52) U.S. Cl.
CPC ........... *G16B 20/10* (2019.02); *C12Q 1/6869* (2013.01); *G16B 20/00* (2019.02); *G16B 20/20* (2019.02); *G16B 30/00* (2019.02); *G16B 40/00* (2019.02); *G16B 40/30* (2019.02)

(58) Field of Classification Search
None
See application file for complete search history.

(56) References Cited

U.S. PATENT DOCUMENTS

| | | | |
|---|---|---|---|
| 5,840,484 A | 11/1998 | Seilhamer et al. | |
| 6,434,542 B1 | 8/2002 | Farmen et al. | |
| 6,586,251 B2 | 7/2003 | Economides et al. | |
| 6,596,541 B2 | 7/2003 | Murphy et al. | |
| 6,658,396 B1 | 12/2003 | Tang et al. | |
| 6,703,228 B1 | 3/2004 | Landers et al. | |
| 6,909,971 B2 | 6/2005 | Toivonen et al. | |
| 6,955,883 B2 | 10/2005 | Margus et al. | |
| 7,065,451 B2 | 6/2006 | Garner et al. | |
| 7,105,348 B2 | 9/2006 | Murphy et al. | |
| 7,107,155 B2 | 9/2006 | Frudakis | |
| 7,213,009 B2 | 5/2007 | Pestotnik et al. | |
| 7,232,656 B2 | 6/2007 | Balasubramanian et al. | |
| 7,324,928 B2 | 1/2008 | Kitchen et al. | |
| 7,424,371 B2 | 9/2008 | Kamentsky | |
| 7,461,006 B2 | 12/2008 | Gogolak | |
| 7,529,685 B2 | 5/2009 | Davies et al. | |
| 7,622,271 B2 | 11/2009 | Kennedy et al. | |
| 7,640,113 B2 | 12/2009 | Frudakis et al. | |
| 7,698,117 B2 | 4/2010 | Usuka et al. | |
| 7,702,468 B2 | 4/2010 | Chinitz et al. | |
| 7,734,656 B2 | 6/2010 | Bessette et al. | |
| 7,809,539 B2 | 10/2010 | Brocklebank et al. | |
| 7,809,660 B2 | 10/2010 | Friedlander et al. | |
| 7,820,378 B2 | 10/2010 | van den Boom et al. | |
| 7,840,512 B2 | 11/2010 | Pandya et al. | |
| 7,912,650 B2 | 3/2011 | Kato et al. | |
| 7,912,674 B2 | 3/2011 | Killoren Clark et al. | |
| 7,937,225 B2 | 5/2011 | Mishra et al. | |
| 7,957,913 B2 | 6/2011 | Chinitz et al. | |
| 7,979,215 B2 | 7/2011 | Sampas | |
| 7,996,157 B2 | 8/2011 | Zabeau et al. | |
| 8,010,295 B1 | 8/2011 | Magness et al. | |
| 8,050,870 B2 | 11/2011 | Heckerman et al. | |

(Continued)

FOREIGN PATENT DOCUMENTS

| | | |
|---|---|---|
| WO | WO-2012/006291 A2 | 1/2012 |
| WO | WO-2012/051346 A1 | 4/2012 |

(Continued)

OTHER PUBLICATIONS

Heng Wang et al. "Copy number variation detection using next generation sequencing read counts," (BMC Bioinformatics vol. 15 (2014) pp. 1-14).*

(Continued)

*Primary Examiner* — Anna Skibinsky
(74) *Attorney, Agent, or Firm* — Ballard Spahr LLP

(57) ABSTRACT

Methods and systems for determining copy number variants are disclosed. An example method can comprise applying a sample grouping technique to select reference coverage data, normalizing sample coverage data comprising a plurality of genomic regions, and fitting a mixture model to the normalized sample coverage data based on the selected reference coverage data. An example method can comprise identifying one or more copy number variants (CNVs) according to a Hidden Markov Model (HMM) based on the normalized sample coverage data and the fitted mixture model. An example method can comprise outputting the one or more copy number variants.

20 Claims, 14 Drawing Sheets

(56) References Cited

U.S. PATENT DOCUMENTS

| | | |
|---|---|---|
| 8,051,033 B2 | 11/2011 | Kenedy et al. |
| 8,078,407 B1 | 12/2011 | Brown |
| 8,095,389 B2 | 1/2012 | Dalton et al. |
| 8,122,073 B2 | 2/2012 | Jung et al. |
| 8,140,270 B2 | 3/2012 | Kingsmore et al. |
| 8,190,373 B2 | 5/2012 | Huang et al. |
| 8,195,415 B2 | 6/2012 | Fan et al. |
| 8,296,116 B2 | 10/2012 | Solomon |
| 8,315,957 B2 | 11/2012 | Heckerman et al. |
| 8,326,648 B2 | 12/2012 | Kenedy et al. |
| 8,335,652 B2 | 12/2012 | Soykan et al. |
| 8,340,950 B2 | 12/2012 | Avey |
| 8,367,333 B2 | 2/2013 | Gudbjartsson et al. |
| 8,372,584 B2 | 2/2013 | Shoemaker et al. |
| 8,380,539 B2 | 2/2013 | Linder et al. |
| 8,428,886 B2 | 4/2013 | Wong et al. |
| 8,429,105 B2 | 4/2013 | Jacobson |
| 8,463,554 B2 | 6/2013 | Hon et al. |
| 8,489,334 B2 | 7/2013 | Chen et al. |
| 8,510,057 B1 | 8/2013 | Avey et al. |
| 8,515,679 B2 | 8/2013 | Rabinowitz et al. |
| 8,554,488 B2 | 10/2013 | Wigler et al. |
| 8,589,175 B2 | 11/2013 | Glauser et al. |
| 8,589,437 B1 | 11/2013 | Khomenko et al. |
| 8,594,944 B2 | 11/2013 | Piper et al. |
| 8,620,594 B2 | 12/2013 | Silver |
| 8,639,446 B1 | 1/2014 | Stupp |
| 8,639,639 B2 | 1/2014 | Jamil et al. |
| 8,655,599 B2 | 2/2014 | Chinitz et al. |
| 8,676,608 B2 | 3/2014 | Oesterheld et al. |
| 8,700,337 B2 | 4/2014 | Dudley et al. |
| 8,706,422 B2 | 4/2014 | Lo et al. |
| 8,718,950 B2 | 5/2014 | Worthey et al. |
| 8,725,418 B2 | 5/2014 | Aerts et al. |
| 8,725,422 B2 | 5/2014 | Halpern et al. |
| 8,731,956 B2 | 5/2014 | Bejjani et al. |
| 8,738,297 B2 | 5/2014 | Sorenson et al. |
| 8,738,300 B2 | 5/2014 | Porreca et al. |
| 8,793,245 B2 | 7/2014 | Kwete |
| 8,795,963 B2 | 8/2014 | Holm et al. |
| 8,796,182 B2 | 8/2014 | Steinthorsdottir et al. |
| 8,812,243 B2 | 8/2014 | Cardonha et al. |
| 8,814,790 B2 | 8/2014 | Eisenhandler et al. |
| 8,818,735 B2 | 8/2014 | Braun et al. |
| 8,828,657 B2 | 9/2014 | Rafnar et al. |
| 8,855,938 B2 | 10/2014 | Friedlander et al. |
| 8,862,410 B2 | 10/2014 | Hatchwell et al. |
| 8,951,735 B2 | 2/2015 | Stacey et al. |
| 8,954,337 B2 | 2/2015 | Tebbs et al. |
| 8,996,318 B2 | 3/2015 | Beatty et al. |
| 9,002,682 B2 | 4/2015 | Kasabov |
| 9,092,391 B2 | 7/2015 | Stephan et al. |
| 9,098,523 B2 | 8/2015 | Bhola et al. |
| 9,111,028 B2 | 8/2015 | Mrazek et al. |
| 9,128,861 B2 | 9/2015 | Bartha et al. |
| 9,141,755 B2 | 9/2015 | Mizuguchi et al. |
| 9,141,913 B2 | 9/2015 | Kupershmidt et al. |
| 9,165,253 B2 | 10/2015 | Cleary et al. |
| 9,177,099 B2 | 11/2015 | Ganeshalingam et al. |
| 9,183,496 B2 | 11/2015 | Harris et al. |
| 9,201,916 B2 | 12/2015 | Doddavula et al. |
| 9,213,944 B1 | 12/2015 | Do et al. |
| 9,215,162 B2 | 12/2015 | Ganeshalingam et al. |
| 9,218,450 B2 | 12/2015 | Chen et al. |
| 9,228,233 B2 | 1/2016 | Kennedy et al. |
| 9,298,804 B2 | 3/2016 | Nizzari et al. |
| 9,309,570 B2 | 4/2016 | Song et al. |
| 9,418,203 B2 | 8/2016 | Pham et al. |
| 9,449,143 B2 | 9/2016 | Vockley et al. |
| 9,483,610 B2 | 11/2016 | McMillen et al. |
| 9,504,428 B1 | 11/2016 | Gelbman et al. |
| 9,547,749 B2 | 1/2017 | OBrien et al. |
| 9,552,458 B2 | 1/2017 | White et al. |
| 9,589,104 B2 | 3/2017 | Heywood et al. |
| 9,600,627 B2 | 3/2017 | Torkamani et al. |
| 9,633,166 B2 | 4/2017 | Kupershmidt et al. |
| 9,652,587 B2 | 5/2017 | Sanborn et al. |
| 9,670,530 B2 | 6/2017 | Kostem et al. |
| 10,395,759 B2 | 8/2019 | Reid et al. |
| 2001/0034023 A1 | 10/2001 | Stanton et al. |
| 2002/0082869 A1 | 6/2002 | Anderson |
| 2002/0133495 A1 | 9/2002 | Rienhoff et al. |
| 2002/0155467 A1 | 10/2002 | Escary |
| 2002/0187496 A1 | 12/2002 | Andersson et al. |
| 2002/0197632 A1 | 12/2002 | Moskowitz |
| 2003/0092040 A1 | 5/2003 | Bader et al. |
| 2003/0101000 A1 | 5/2003 | Bader et al. |
| 2003/0104470 A1 | 6/2003 | Fors et al. |
| 2003/0108938 A1 | 6/2003 | Pickar et al. |
| 2003/0113756 A1 | 6/2003 | Mertz |
| 2003/0138778 A1 | 7/2003 | Garner et al. |
| 2003/0195707 A1 | 10/2003 | Schork et al. |
| 2003/0211504 A1 | 11/2003 | Fechtel et al. |
| 2004/0053251 A1 | 3/2004 | Pericak-Vance et al. |
| 2004/0086888 A1 | 5/2004 | Kornblith et al. |
| 2004/0115701 A1 | 6/2004 | Comings et al. |
| 2004/0142325 A1 | 7/2004 | Mintz et al. |
| 2004/0146870 A1 | 7/2004 | Liao et al. |
| 2004/0161779 A1 | 8/2004 | Gingeras |
| 2004/0175700 A1 | 9/2004 | Geesaman |
| 2004/0219567 A1 | 11/2004 | Califano et al. |
| 2004/0248092 A1 | 12/2004 | Vance et al. |
| 2004/0249677 A1 | 12/2004 | Datta et al. |
| 2004/0267458 A1 | 12/2004 | Judson et al. |
| 2005/0019787 A1 | 1/2005 | Berno et al. |
| 2005/0064408 A1 | 3/2005 | Sevon et al. |
| 2005/0086035 A1 | 4/2005 | Peccoud et al. |
| 2005/0176031 A1 | 8/2005 | Sears et al. |
| 2005/0191731 A1 | 9/2005 | Judson et al. |
| 2005/0214811 A1 | 9/2005 | Margulies et al. |
| 2005/0250098 A1 | 11/2005 | Toivonen et al. |
| 2005/0256649 A1 | 11/2005 | Roses |
| 2005/0272057 A1 | 12/2005 | Abrahamsen et al. |
| 2006/0173663 A1 | 8/2006 | Langheier et al. |
| 2006/0286566 A1 | 12/2006 | Lapidus et al. |
| 2007/0027636 A1 | 2/2007 | Rabinowitz |
| 2007/0042369 A1 | 2/2007 | Reese et al. |
| 2007/0082353 A1 | 4/2007 | Hiraoka et al. |
| 2007/0112585 A1 | 5/2007 | Breiter et al. |
| 2007/0174253 A1 | 7/2007 | Hodnett et al. |
| 2007/0196850 A1 | 8/2007 | Kennedy et al. |
| 2007/0276610 A1 | 11/2007 | Berg |
| 2008/0091358 A1 | 4/2008 | Taylor |
| 2008/0281818 A1 | 11/2008 | Tenenbaum et al. |
| 2008/0311574 A1 | 12/2008 | Manne et al. |
| 2009/0011407 A1 | 1/2009 | Liu et al. |
| 2009/0012928 A1 | 1/2009 | Lussier et al. |
| 2009/0035279 A1 | 2/2009 | Thorleifsson et al. |
| 2009/0098547 A1 | 4/2009 | Ghosh |
| 2009/0125246 A1 | 5/2009 | Ruiz Laza |
| 2009/0137402 A1 | 5/2009 | Wang et al. |
| 2009/0181380 A1 | 7/2009 | Belouchi et al. |
| 2009/0198519 A1 | 8/2009 | McNamar |
| 2009/0240441 A1 | 9/2009 | Lapidus |
| 2009/0299645 A1 | 12/2009 | Colby et al. |
| 2010/0114956 A1 | 5/2010 | McElfresh et al. |
| 2010/0130526 A1 | 5/2010 | Glinsky |
| 2010/0143921 A1 | 6/2010 | Sadee et al. |
| 2010/0184037 A1 | 7/2010 | Plass et al. |
| 2010/0216655 A1 | 8/2010 | Sulem |
| 2010/0317726 A1 | 12/2010 | Figg et al. |
| 2011/0004616 A1 | 1/2011 | Miyao |
| 2011/0014607 A1 | 1/2011 | Jirtle et al. |
| 2011/0020320 A1 | 1/2011 | Gudmundsson et al. |
| 2011/0045997 A1 | 2/2011 | Tejedor Hernandez et al. |
| 2011/0111419 A1 | 5/2011 | Stefansson et al. |
| 2011/0202486 A1 | 8/2011 | Fung et al. |
| 2011/0212855 A1 | 9/2011 | Rafnar et al. |
| 2011/0230366 A1 | 9/2011 | Gudmundsson et al. |
| 2011/0251243 A1 | 10/2011 | Tucker et al. |
| 2011/0257896 A1 | 10/2011 | Dowds et al. |
| 2011/0287946 A1 | 11/2011 | Gudmundsson et al. |
| 2012/0010866 A1 | 1/2012 | Ramnarayan |
| 2012/0016594 A1 | 1/2012 | Christman et al. |

(56) References Cited

U.S. PATENT DOCUMENTS

| | | |
|---|---|---|
| 2012/0078901 A1 | 3/2012 | Conde |
| 2012/0109615 A1 | 5/2012 | Yun et al. |
| 2012/0110013 A1 | 5/2012 | Conde et al. |
| 2012/0122698 A1 | 5/2012 | Stacey et al. |
| 2012/0143512 A1 | 6/2012 | Reese et al. |
| 2012/0173153 A1 | 7/2012 | Elango et al. |
| 2012/0191366 A1 | 7/2012 | Pearson et al. |
| 2012/0215459 A1 | 8/2012 | Stef et al. |
| 2012/0215463 A1 | 8/2012 | Brodzik |
| 2012/0310539 A1 | 12/2012 | Crockett et al. |
| 2012/0330559 A1 | 12/2012 | Jiang et al. |
| 2013/0035864 A1 | 2/2013 | Stupp et al. |
| 2013/0039548 A1 | 2/2013 | Nielsen et al. |
| 2013/0080365 A1 | 3/2013 | Dewey et al. |
| 2013/0090859 A1 | 4/2013 | Palsson et al. |
| 2013/0184161 A1 | 7/2013 | Kingsmore et al. |
| 2013/0184999 A1 | 7/2013 | Ding |
| 2013/0212125 A1 | 8/2013 | Wierenga et al. |
| 2013/0224739 A1 | 8/2013 | Thorleifsson et al. |
| 2013/0226468 A1 | 8/2013 | Skinner et al. |
| 2013/0226621 A1 | 8/2013 | Van Der Zaag et al. |
| 2013/0245958 A1 | 9/2013 | Forster et al. |
| 2013/0246033 A1 | 9/2013 | Heckerman et al. |
| 2013/0259847 A1 | 10/2013 | Vishnudas et al. |
| 2013/0261984 A1 | 10/2013 | Eberle et al. |
| 2013/0273543 A1 | 10/2013 | Gudmundsson et al. |
| 2013/0296175 A1 | 11/2013 | Rafnar et al. |
| 2013/0296193 A1 | 11/2013 | Choi et al. |
| 2013/0297221 A1 | 11/2013 | Johnson et al. |
| 2013/0309666 A1 | 11/2013 | Deciu et al. |
| 2013/0316915 A1 | 11/2013 | Halpern et al. |
| 2013/0332081 A1 | 12/2013 | Reese et al. |
| 2013/0338012 A1 | 12/2013 | Sulem et al. |
| 2013/0345066 A1 | 12/2013 | Brinza et al. |
| 2014/0024029 A1 | 1/2014 | Mrazek |
| 2014/0040264 A1 | 2/2014 | Varadan et al. |
| 2014/0046696 A1 | 2/2014 | Higgins et al. |
| 2014/0046926 A1 | 2/2014 | Walton |
| 2014/0066317 A1 | 3/2014 | Talasaz |
| 2014/0067355 A1 | 3/2014 | Noto et al. |
| 2014/0087961 A1 | 3/2014 | Sulem et al. |
| 2014/0088942 A1 | 3/2014 | Li et al. |
| 2014/0089009 A1 | 3/2014 | Van Criekinge et al. |
| 2014/0100792 A1 | 4/2014 | Deciu et al. |
| 2014/0114582 A1 | 4/2014 | Mittelman et al. |
| 2014/0114584 A1 | 4/2014 | Bruestle |
| 2014/0115515 A1 | 4/2014 | Adams et al. |
| 2014/0143188 A1 | 5/2014 | Mackey et al. |
| 2014/0153801 A1 | 6/2014 | Sarkozy et al. |
| 2014/0200824 A1 | 7/2014 | Pancoska |
| 2014/0206006 A1 | 7/2014 | Xu et al. |
| 2014/0214331 A1 | 7/2014 | Kowalczyk et al. |
| 2014/0214333 A1 | 7/2014 | Plattner et al. |
| 2014/0214334 A1 | 7/2014 | Plattner et al. |
| 2014/0222349 A1 | 8/2014 | Higgins et al. |
| 2014/0229117 A1 | 8/2014 | Halpern et al. |
| 2014/0229495 A1 | 8/2014 | Makkapati et al. |
| 2014/0235456 A1 | 8/2014 | Garner, Jr. et al. |
| 2014/0244556 A1 | 8/2014 | Saleh et al. |
| 2014/0247184 A1 | 9/2014 | Wendel |
| 2014/0248692 A1 | 9/2014 | Ace et al. |
| 2014/0249764 A1 | 9/2014 | Kumar et al. |
| 2014/0274745 A1 | 9/2014 | Chen et al. |
| 2014/0278133 A1 | 9/2014 | Chen et al. |
| 2014/0278461 A1 | 9/2014 | Artz |
| 2014/0287934 A1 | 9/2014 | Szelinger et al. |
| 2014/0303901 A1 | 10/2014 | Sadeh |
| 2014/0310215 A1 | 10/2014 | Kadis |
| 2014/0350954 A1 | 11/2014 | Ellis et al. |
| 2014/0359422 A1 | 12/2014 | Bassett, Jr. et al. |
| 2014/0365243 A1 | 12/2014 | Varadan et al. |
| 2014/0372953 A1 | 12/2014 | Laurance |
| 2015/0024948 A1 | 1/2015 | Dugas et al. |
| 2015/0046191 A1 | 2/2015 | Futscher de Deus et al. |
| 2015/0051116 A1 | 2/2015 | Kim |
| 2015/0056619 A1 | 2/2015 | Li et al. |
| 2015/0066381 A1 | 3/2015 | Kurai |
| 2015/0066385 A1 | 3/2015 | Schnall-Levin et al. |
| 2015/0073719 A1 | 3/2015 | Glynias et al. |
| 2015/0073724 A1 | 3/2015 | Ashutosh et al. |
| 2015/0081323 A1 | 3/2015 | Jackson et al. |
| 2015/0095064 A1 | 4/2015 | Schols |
| 2015/0105267 A1 | 4/2015 | Shendure et al. |
| 2015/0105270 A1 | 4/2015 | Floratos |
| 2015/0120322 A1 | 4/2015 | Hoffman et al. |
| 2015/0142331 A1 | 5/2015 | Beim et al. |
| 2015/0169828 A1 | 6/2015 | Spector |
| 2015/0178445 A1 | 6/2015 | Cibulskis et al. |
| 2015/0193578 A1 | 7/2015 | Kiel et al. |
| 2015/0197785 A1 | 7/2015 | Carter et al. |
| 2015/0199472 A1 | 7/2015 | Kurai |
| 2015/0199473 A1 | 7/2015 | Kurai |
| 2015/0199474 A1 | 7/2015 | Kurai |
| 2015/0199475 A1 | 7/2015 | Kurai |
| 2015/0205914 A1 | 7/2015 | Richards et al. |
| 2015/0220687 A1 | 8/2015 | An |
| 2015/0227697 A1 | 8/2015 | Nelson et al. |
| 2015/0228041 A1 | 8/2015 | Naley et al. |
| 2015/0248522 A1 | 9/2015 | Guturu et al. |
| 2015/0248525 A1 | 9/2015 | Ury et al. |
| 2015/0254397 A1 | 9/2015 | Rogan et al. |
| 2015/0261913 A1 | 9/2015 | Dewey et al. |
| 2015/0294063 A1 | 10/2015 | Kalalakaran et al. |
| 2015/0310163 A1 | 10/2015 | Kingsmore et al. |
| 2015/0310165 A1 | 10/2015 | Mann |
| 2015/0310228 A1 | 10/2015 | Benz et al. |
| 2015/0315645 A1 | 11/2015 | Gaasterland et al. |
| 2015/0317432 A1 | 11/2015 | Silver et al. |
| 2015/0324519 A1 | 11/2015 | Liu |
| 2015/0347676 A1 | 12/2015 | Zhao et al. |
| 2015/0356243 A1 | 12/2015 | Andreassen et al. |
| 2015/0363549 A1 | 12/2015 | Kimura |
| 2015/0367145 A1 | 12/2015 | Sjolund et al. |
| 2015/0376700 A1 | 12/2015 | Schnall-Levin et al. |
| 2015/0379193 A1 | 12/2015 | Bassett, Jr. et al. |
| 2016/0004814 A1 | 1/2016 | Stamatoyannopoulos |
| 2016/0017412 A1 | 1/2016 | Srinivasan et al. |
| 2016/0024591 A1 | 1/2016 | Xu et al. |
| 2016/0026753 A1 | 1/2016 | Krishnaswami et al. |
| 2016/0026772 A1 | 1/2016 | Plante et al. |
| 2016/0034667 A1 | 2/2016 | Rosenblatt et al. |
| 2016/0040239 A1 | 2/2016 | Sadee et al. |
| 2016/0048608 A1 | 2/2016 | Frieden et al. |
| 2016/0070854 A1 | 3/2016 | Wong et al. |
| 2016/0070855 A1 | 3/2016 | Sanborn et al. |
| 2016/0078094 A1 | 3/2016 | Popescu et al. |
| 2016/0078169 A1 | 3/2016 | Namkung et al. |
| 2016/0092631 A1 | 3/2016 | Yandell et al. |
| 2016/0098519 A1 | 4/2016 | Zwir |
| 2016/0103919 A1 | 4/2016 | Boyce |
| 2016/0140289 A1 | 5/2016 | Gibiansky et al. |
| 2016/0153032 A9 | 6/2016 | Rosenthal et al. |
| 2016/0154928 A1 | 6/2016 | Zeskind et al. |
| 2016/0186253 A1 | 6/2016 | Talasaz et al. |
| 2016/0196382 A1 | 7/2016 | Kim et al. |
| 2016/0201134 A1 | 7/2016 | Liao et al. |
| 2016/0203196 A1 | 7/2016 | Schnall-Levin et al. |
| 2016/0203287 A1 | 7/2016 | Chen et al. |
| 2016/0210401 A1 | 7/2016 | Kim et al. |
| 2016/0224722 A1 | 8/2016 | Reese et al. |
| 2016/0224730 A1 | 8/2016 | Yu et al. |
| 2016/0232291 A1 | 8/2016 | Kyriazopoulou-Panagiotopoulou et al. |
| 2016/0239603 A1 | 8/2016 | Brown |
| 2016/0253452 A1 | 9/2016 | Karbass et al. |
| 2016/0253770 A1 | 9/2016 | Downs et al. |
| 2016/0259880 A1 | 9/2016 | Semenyuk |
| 2016/0259886 A1 | 9/2016 | Li et al. |
| 2016/0273049 A1 | 9/2016 | Velculescu et al. |
| 2016/0281166 A1 | 9/2016 | Bhattacharjee et al. |
| 2016/0283407 A1 | 9/2016 | Van Rooyen et al. |
| 2016/0283484 A1 | 9/2016 | Chandratillake et al. |
| 2016/0298185 A1 | 10/2016 | Shukla et al. |
| 2016/0300012 A1 | 10/2016 | Barber et al. |

(56) References Cited

U.S. PATENT DOCUMENTS

| | | |
|---|---|---|
| 2016/0300013 A1 | 10/2016 | Ashutosh et al. |
| 2016/0306921 A1 | 10/2016 | Kurai |
| 2016/0314245 A1 | 10/2016 | Silver et al. |
| 2016/0319335 A1 | 11/2016 | Deciu et al. |
| 2016/0333411 A1 | 11/2016 | Harper |
| 2016/0340722 A1 | 11/2016 | Platt |
| 2016/0342732 A1 | 11/2016 | Popovic et al. |
| 2016/0342733 A1 | 11/2016 | Reid et al. |
| 2016/0342737 A1 | 11/2016 | Kaye |
| 2016/0370961 A1 | 12/2016 | Merel |
| 2016/0371429 A1 | 12/2016 | Patil et al. |
| 2016/0371431 A1 | 12/2016 | Haque et al. |
| 2016/0374600 A1 | 12/2016 | Short et al. |
| 2017/0004256 A1 | 1/2017 | Miyashita et al. |
| 2017/0017717 A1 | 1/2017 | Kimura |
| 2017/0017752 A1 | 1/2017 | Noto et al. |
| 2017/0032081 A1 | 2/2017 | Agrawal et al. |
| 2017/0061070 A1 | 3/2017 | Kingsmore et al. |
| 2017/0068826 A1 | 3/2017 | Dimitrova et al. |
| 2017/0073755 A1 | 3/2017 | Tiwari et al. |
| 2017/0076046 A1 | 3/2017 | Barnes et al. |
| 2017/0076050 A1 | 3/2017 | Soon-Shiong |
| 2017/0091382 A1 | 3/2017 | Yun et al. |
| 2017/0098053 A1 | 4/2017 | Pandey et al. |
| 2017/0107576 A1 | 4/2017 | Babiarz et al. |
| 2017/0109471 A1 | 4/2017 | Ariyaratne et al. |
| 2017/0116379 A1 | 4/2017 | Scott et al. |
| 2017/0132357 A1 | 5/2017 | Brewerton et al. |
| 2017/0132362 A1 | 5/2017 | Skinner et al. |
| 2017/0154154 A1 | 6/2017 | Daly et al. |
| 2017/0169160 A1 | 6/2017 | Hu et al. |
| 2017/0169163 A1 | 6/2017 | Shomron et al. |
| 2017/0175206 A1 | 6/2017 | Xu et al. |
| 2017/0198348 A1 | 7/2017 | Namkung |
| 2017/0199960 A1 | 7/2017 | Ghose et al. |
| 2017/0202519 A1 | 7/2017 | Kuo |
| 2017/0211205 A1 | 7/2017 | Murray |
| 2017/0213011 A1 | 7/2017 | Hoffman et al. |
| 2017/0213127 A1 | 7/2017 | Duncan |
| 2017/0233806 A1 | 8/2017 | Maxwell et al. |

FOREIGN PATENT DOCUMENTS

| | | |
|---|---|---|
| WO | WO-2013/102441 A1 | 7/2013 |
| WO | WO2014024142 | 2/2014 |
| WO | WO-2014/121128 A1 | 8/2014 |
| WO | WO-2014/145234 A2 | 9/2014 |
| WO | WO-2014/145503 A2 | 9/2014 |
| WO | WO-2015/013191 A1 | 1/2015 |
| WO | WO-2015/051163 A2 | 4/2015 |
| WO | WO-2015/148776 A1 | 10/2015 |
| WO | WO-2015/173435 A1 | 11/2015 |
| WO | WO-2015/184404 A1 | 12/2015 |
| WO | WO-2015/191562 A1 | 12/2015 |
| WO | WO-2016/038220 A1 | 3/2016 |
| WO | WO-2016/055971 A2 | 4/2016 |
| WO | WO-2016/061570 A1 | 4/2016 |
| WO | WO-2016/062713 A1 | 4/2016 |
| WO | WO-2016/064995 A1 | 4/2016 |
| WO | PCT/US2016/032484 | 5/2016 |
| WO | WO-2016/083949 A1 | 6/2016 |
| WO | WO-2016/122318 A1 | 8/2016 |
| WO | WO-2016/124600 A1 | 8/2016 |
| WO | WO-2016/139534 A2 | 9/2016 |
| WO | WO-2016/141127 A1 | 9/2016 |
| WO | WO-2016/141214 A1 | 9/2016 |
| WO | WO-2016/154254 A1 | 9/2016 |
| WO | WO-2016/154584 A1 | 9/2016 |
| WO | WO-2016/172801 A1 | 11/2016 |
| WO | WO-2016/179049 A1 | 11/2016 |
| WO | WO-2016/183659 A1 | 11/2016 |
| WO | WO-2016/187051 A1 | 11/2016 |
| WO | WO-2016/201564 A1 | 12/2016 |
| WO | WO-2016/203457 A1 | 12/2016 |
| WO | WO-2017/009372 A2 | 1/2017 |
| WO | PCT/US2017/017734 | 2/2017 |
| WO | WO-2017/024138 A1 | 2/2017 |
| WO | PCT/US2017/024810 | 3/2017 |
| WO | WO-2017/042831 A2 | 3/2017 |
| WO | WO-2017/049214 A1 | 3/2017 |
| WO | WO-2017/064142 A1 | 4/2017 |
| WO | WO-2017/065959 A2 | 4/2017 |
| WO | WO-2017/100794 A1 | 6/2017 |
| WO | WO-2017/116123 A1 | 7/2017 |
| WO | WO-2017/120556 A1 | 7/2017 |
| WO | WO-2017/139801 A1 | 8/2017 |

OTHER PUBLICATIONS

Fromer et al. "Discovery and Statistical Genotyping of Copy-Number Variation from Whole-Exome Sequencing Depth" (The American Journal of Human Genetics, vol. 91 (2021) pp. 597-607).*

Office Action dated Jul. 20, 2020 by the Russian Patent Office for RU Application No. 2017143983, filed on May 13, 2016 (Applicant—37595—(Regeneron Pharmaceuticals, Inc.) (English Translation 5 Pages).

Office Action dated Mar. 30, 2020 by the Israeli Patent Office for IL Application No. 255458, filed on Jun. 11, 2017 (Applicant—37595—(Regeneron Pharmaceuticals, Inc.) (English Translation 3 Pages).

Backenroth et al. (2014) CANOES: detecting rare copy number variants from whole exome sequencing data, Nucleic Acids Res, 42 (12), e97 (9 pages).

Baigent, S. et al., Efficacy and Safety of Cholesterol-Lowering Treatment: Prospective Meta-Analysis of Data from 90,056 Participants in 14 Randomised Trials of Statins. Lancet. 2005; 366(9493): 1267-78.

Benjamini, Yuval, and Speed, Terence P. (2012) Summarizing and correcting the GC content bias in high-throughput sequencing, Nucleic Acids Res, 40 (10), e72 (14 pages).

Benn, M. et al., PCSK9 R46L, Low-Density Lipoprotein Cholesterol Levels, and Risk of Ischemic Hear Disease. J Am Coll Cardiol. 2010; 55:2833-42.

Berg, J.S. et al., An Informatics Approach to Analyzing the Incidentalome. Genet Med. 2013; 15(1):36-44.

Blekhman, R. et al., Natural Selection on Genes that Underline Human Disease Susceptibility. Curr Biol. 2008; 18(12):883-9.

Boettger, L.M. et al., Recurring Exon Deletions in the HP (haptoglobin) Gene Contribute to Lower Blood Cholesterol Levels. Nat Genet. 2016; 48:359-66.

Brand, H. et al., Paired-Duplication Signatures Mark Cryptic Inversions and Other Complex Structural Variation. Am J Hum Genet. 2015; 97(1):170-6.

Brundert, M. et al., Scavenger Receptor CD36 Mediates Uptake of High Density Lipoproteins in Mice and by Cultured Cells. J Lipid Res. 2011; 52(4):745-58.

Carey et al., The Geisinger MyCode Community Health Initiative: an Electronic Health Record-Linked Biobank for Precision Medicine Research. Genes in Medicine. 2016; 18(9):906-13.

Carvalho et al., Inverted Genomic Segments and Complex Triplication Rearrangements are mediated by Inverted Repeats in the Human Genome. Nat Genet. 2011; 43(11):1074-81.

Chance, P.F. et al., DNA Deletion Associated with Hereditary Neuropathy with Liability to Pressure Palsies. Cell. 1993; 72(1):143-51.

Chance, P.F. et al., Two Autosomal Dominant Neuropathies Result from Reciprocal DNA Duplication/Deletion of a Region on Chromosome 17. Hum Mol Genet. 1994; 3:223-8.

Chang, C.C. et al., Second-Generation PLINK: Rising to the Challenge of Larger and Richer Datasets. Gigascience. 2015; 4:7 (16 pages).

Choi, M. et al., Genetic Diagnosis by Whole Exome Capture and Massively Parallel DNA Sequencing. Proc Natl Acad Sci USA. 2009; 106(45):19096-101.

Chong, J.X. et al., The Genetic Basis of Mandelian Phenotypes: Discoveries, Challenges, and Opportunities. Am J Hum Genet. 2015; 97(2):199-215.

(56) References Cited

OTHER PUBLICATIONS

Chou, J.Y. et al., Type I Glycogen Storage Diseases: Disorders of the Glucose-6-Phosphatase Complex. Curr Mol Med. 2002; 2(2):121-43.
Cingolani, P. et al., A Program for Annotating and Predicting the Effects of Single Nucleotide Polymorphisms, SnpEff. Fly (Austin). 2012; 6(2):80-92.
Coe et al. (2014) Refining analyses of copy number variation identities specific genes associated with developmental delay. Nat Genet, 46 (10): 1063-71.
Cohen, J.C. et al., Sequence Variations in PCCK9, Low LDL, and Protection Against Coronary Heart Disease. N Engl J Med. 2006; 354(12):1264-72.
Conrad, D.F. et al., Origins and Functional Impact of Copy Number variation in the Human Genome. Nature. 2010; 464(7289):704-12.
Coram, M.A., Genome-wide Characterization of Shared and Distant Genetic Components that Influence Blood Lipid Levels in Ethnically Diverse Human Populations. Am J Hum Genet. 2013; 92:904.
Cousin, The Next Generation of CNV Detection,Genetic Engineering and Biotechnology News, Jan. 1, 2018 (vol. 38, No. 1) https://www.genengnews.com/magazine/306/the-next-generation-of-cnv-detection/.
De Cid, R. et al., Deletion of the Late Cornified Envelope (LCE) 3B and 3C Genes as a Susceptibility Factor for Psoriasis. Nat Genet. 2009; 41(2):211-5.
Denny, J.C. et al., Systematic Comparison of Phenome-wide Association Study of Electronic Medical Record Data and Genome-wide Association Study Data. Nature Biotechnol. 2013; 31(12):1102-11.
DiVincenzo, C. et al., The Allelic Spectrum of Charcot-Marie-Tooth Disease in Over 17,000 Individuals with Neuropathy. Mol Genet Genomic Med. 2014; 2(6):522-9.
Do, R. et al., Exome Sequencing Identifies Rare LDLR and APOA5 Alleles Conferring Risk for Myocardial Infarction. Nature. 2015; 518(7537):102-6.
Elbers, C.C. et al., Gene-Centric Meta-Analysis of Lipid Traits in African, East Asian and Hispanic Populations. PLoS One. 2012; 7(12):e50198 (14 pages).
Ferreira, M.A. and S.M. Purcell, The Multivariate Test of Association. Bioinformatics. 2009; 25(1):132-3.
Final Rejection dated Jan. 25, 2018 to the USPTO for U.S. Appl. No. 14/714,949, filed May 18, 2015, and published as US 2016-0342733 A1 on Nov. 24, 2016 (Applicant—Jeffrey Reid ) (10 pages).
Fromer et al., (2012) "Discovery and statistical genotyping of copy-number variation from whole-exome sequencing depth," Am J Hum Genet 91 (4), 597-607.
Georgi, B. et al., From Mouse to Human: Evolutionary Genomics Analysis of Human Orthologs of Essential Genes. PLoS Genet. 2013; 9(5):e1003484 (10 pages).
Girirajan, S. et al., A Recurrent 16p12.1 Microdeletion Supports a Two-Hit Model for Severe Developmental Delay. Nat Genet. 2010; 42:203-9.
Gottesman, O. et al., Can Genetic Pleiotropy Replicate Common Clinical Constellations of Cardiovascular Disease and Risk? PLoS One. 2012; 7(9):e46419 (9 pages).
Green, R.C. et al., ACMG Recommendations for Reporting of Incidental Findings in Clinical Exome and Genome Sequencing. Genet Med. 2013; 15(7):565-74.
Gudbjartsson, D.F. et al., Large-Scale Whole-Genome Sequencing of the Icelandic Population. Nat Genet. 2015; 47(5):435-44.
Handsaker et al. (2015) Large multiallelic copy number variations in humans. Nat Genet, 47 (3), 296-303.
Heinzen, E.L. et al., Rare Deletions at 16p13.11 Predispose to a Diverse Spectrum of Sporadic Epilepsy Syndromes. Am J Hum Genet. 2010; 86(5):707-18.
Hirayasu, K. and H. Arase, Functional and Genetic Diversity of Leukocyte Immunoglobulin-like Receptor and Implication for Disease Associations. J Hum Genet. 2015; 60(11):703-8.
Holm, H. et al., A Rare Variant in MYH6 is Associated with High Risk of Sick Sinus Syndrome. Nat Genet. 2011; 43:316-20.
Hoogendijk, J.E. et al., De-novo Mutation in Hereditary Motor and Sensory Neuropathy Type I. Lancet. 1992; 339(8801):1081-2.
Huff, C.D. et al., Maximum-lielihood Estimation of Recent Shared Ancestry (ERSA). Genome Res. 2011; 21(5):768-74.
Hughes, A.E. et al., A Common CFH Haplotype, with Deletion of CFHR1 and CFHR3, is Associated with Lower Risk of Age-Related Macular Degeneration. Nat Genet. 2006; 38(10):1173.
International Preliminary Report on Patentability dated Nov. 21, 2017 by the International Searching Authority for International Application No. PCT/US2016/032484, filed on May 13, 2016 and published as WO 2016/187051 on Nov. 24, 2016 (Applicant—Regeneron Pharmaceuticals, Inc.) (6 Pages).
International Search Report and Written Opinion dated Aug. 17, 2016 by the International Searching Authority for Patent Application No. PCT/2016/032484, which was filed on May 13, 2016 and published as WO 2016/187051 (Inventor—Reid et al.; Applicant—Regeneron Pharmaceuticals, Inc.) (8 pages).
International Search Report and Written Opinion dated Jul. 21, 2017 by the International Searching Authority for Patent Application No. PCT/US2017/017734, which was filed on Feb. 13, 2017 and published as WO 2017/139801 on Aug. 17, 2017 (Inventor—Maxwell et al.; Applicant—Regeneron Pharmaceuticals, Inc.) (13 pages).
International Search Report and Written Opinion dated Sep. 4, 2017 for Patent Application No. PCT/US2017/024810, which was filed on Mar. 29, 2017 and published as WO 2017/172958 on Oct. 5, 2017 (Inventor—Reid et al.; Applicant—Regeneron Pharmaceuticals, Inc.) (18 pages).
Issue Notification dated Aug. 7, 2019 by the USPTO office for U.S. Appl. No. 14/714,949, filed May 18, 2015 and published as US-2016/0342733-A1 on Nov. 24, 2016 (Inventor—Jeffrey Reid) (1 page).
K-d tree, Wikipedia (2018) [retrieved on Apr. 25, 2018] Retrieved from the internet <URL: https://en.wikipedia.org/wiki/K-d_tree>.
Kathiresan, S., A PCSK9 Missense Variant Associated with a Reduced Risk of Early-Onset Myocardial Infarction. N Engl J Med. 2008; 358(21):2299-300.
Kd-trees CMSC 420 (2014) [retrieved on Jan. 19, 2018] Retrieved from the internet <URL: https://www.cs.cmu.edu/-ckingsf/u bioinfo-lectures/kdtrees.pdf>.
Kloosterman, W.P. et al., Characteristics of De Novo Structural Changes in the Human Genome. Genome Res. 2015; 25:792-801.
Korbel, J.O. et al., Paired-End Mapping Reveals Extensive Structural Variation in the Human Genome. Science. 2007; 318(5849):420-6.
Krumm et al. (2012) Copy number variation detection and genotyping from exome sequence data. Genome Res, 22 (8), 1525-32.
Landrum, M.J. et al., ClinVar: Public Archive of Relationships Among Sequence Variation and Human Phenotype. Nucleic Acids Res. 2014; 42:D980-5.
Lange, L.A. et al., Whole-exome Sequencing Identifies Rare and Low-Frequency Coding Variants Associated wth LDL Cholesterol. Am J Hum Genet. 2014; 94(2):233-45.
Layer, R.M. et al., LUMPY: A Probabilistic Framework for Structutral Variant Discovery. Genome Biol. 2014; 15:R84 (19 pages).
Lee, S. et al., Rare-Variant Association Analysis: Study Designs and Statistical Tests. Am J Hum Genet. 2014; 95(1):5-23.
Leigh, S.E. et al., Update and Analysis of the University College London Low Density Lipoprotein Receptor Familial Hypercholesterolemia Database. Ann Hum Genet. 2008; 72(4):485-98.
Lek, M. et al., Analysis of Protein-Coding Genetics Variation in 60,706 Humans. Nature. 2016; 536:285-91.
Li et al. (2009) The Sequence Alignment/Map format and SAMtools. Bioinformatics, 25 (16), 2078-9.
Li, A.H. et al., Analysis of Loss-of-Function Variants and 20 Risk Factor Phenotypes in 8,554 Individuals Identifies Loci Influencing chronic Disease. Nat Genet. 2015; 47(6):640-2.
Li, B. and S.M. Leal, Methods for Detecting Associations with Rare Variants for Common Diseases: Application to Analysis of Sequence Data. Am J Hum Genet. 2008; 83(3):311-21.
Li, H. and R. Durbin, Fast and Accurate Short Read Alignment with Burrows-Wheeler Transform. Bioinformatics. 2009; 25(14):1754-60.
Li, H. et al., The Sequence Alignment/Map Format and SAMtools. Bioinformatics. 2009; 25(16):2078-9.

(56) References Cited

OTHER PUBLICATIONS

Lim, E.T. et al., Distribution and Medical Impact of Loss-of-function Variatns in the Finnish Founder Population. PLoS Genet. 2014; 10(7):e1004494 (12 pages).
Liu, P. et al., Mechanisms for Recurrent and Complex Human Genomic Rearrangements. Curr Opin Genet Dev. 2012; 22(3):211-20.
Loh, P.R. et al., Efficient Bayesian Mixed Model Analysis Increases Association Power in Large Cohorts. Nat Genet. 2015; 47(3):284-90.
Lupski, J.R. et al., DNA Duplication Associated with Charcot-Marie-Tooth Disease Type 1A. Cell. 1991; 66(2):219-32.
Lupski, J.R., Structural Variation Mutagenesis of the Human Genome: Impact on Disease and Evolution. Environ Mol Mutagen. 2015; 56(5):419-36.
MacArthur, D.G. et al., A Systematic Survey of Loss-Function Variants in Human Protein-Coding Genes. Science. 2012; 335(6070):823-8.
MacDonald, J.R. et al., The Database of Genomic Variants: a Curated Collection of Structural Variation in the Human Genome. Nucleic Acids Res. 2013; 42(Database Issue):D986-92.
Mahmud et al., "Fast MCMC sampling for hidden markov models to determine copy number variations" BMC Bioinformatics 2011 12:428.
Mahmud, P. et al., Fast MCMC Sampling for Hidden Markov Models to Determine Copy Number Variations. BMC Bioinformatics. 2011; 12(1):428 (17 pages).
McCarthy, S.E. et al., Microduplications of 16p11.2 are Associated with Schizophrenia. Nat Genet. 2009;41(11):1223-7.
McKenna, A. et al., The Genome Analysis Toolkit: A MapReduce Framework for Analyzing Next-Generation DNA Sequencing Data. Genome Res. 2010; 20(9):1297-303.
Mefford, H.C. et al., Recurrent Rearrangements of Chromosome 1q21.1 and Variable Pediatric Phenotypes. N Engl J Med. 2008; 359:1685-99.
Meretoja, P. et al., Epidemiology of Hereditary Neuropathy with Liability to Pressure Palsies (HNPP) in South Western Finland. Neuromuscul Disord. 1997; 7(8):529-32.
Mills, R.E. et al., Mapping Copy Number Variation by Population-Scale Genome Sequencing. Nature. 2011; 470: 59-65.
Myocardial Infarction Genetics Consortium Investigators, Inactivating Mutations in NPC1L1 and Protection from Coronary Heart Disease. N Engl J Med. 2014; 371:2072.
Newman, S. et al., Next-Generation Sequencing of Duplication CNVs reseals that Most Are Tandem and Some Create Fusion Genes in Breakpoints. Am J Hum Genet. 2015; 96(2):208.
Non Final Rejection dated Jan. 10, 2019 by the USPTO office for U.S. Appl. No. 14/714,949, filed May 18, 2015 and published as US-2016/0342733-A1 on Nov. 24, 2016 (Inventor—Jeffrey Reid) (9 pages).
Non Final was issued on Jun. 22, 2017 by the USPTO for U.S. Appl. No. 14/714,949, filed May 18, 2015, and published as US 2016-0342733 A1 on Nov. 24, 2016 (Applicant—Jeffrey Reid ) (9 pages).
Non-Final Office Action dated Jun. 22, 2017 by the U.S. Patent and Trademark Office for U.S. Appl. No. 14/714,949, filed May 18, 2015 and published as US 2016/0342733 on Nov. 24, 2016 (Inventor—Reid et al.; Applicant—Regeneron Pharmaceuticals, Inc.) (9 pages).
Notice of Allowance dated May 1, 2019 by the USPTO office for U.S. Appl. No. 14/714,949, filed May 18, 2015 and published as US-2016/0342733-A1 on Nov. 24, 2016 (Inventor—Jeffrey Reid) (8 pages).
O'Dushlaine, C.T. et al., Population Structure and Genome-Wide Patterns of Variation in Ireland and Britain. Eur J Hum Genet. 2010; 18(11):1248-54.
Ordóñez, D. et al., Multiple Sclerosis Associates with LILRA3 Deletion in Spanish Patients. Genes and Immunity. 2009; 10:579.
Pabinger, S. et al.; A Survey of Tools for Variant Analysis of Next-Generation Genome Sequencing Data. Briefings Bioinformatics. 2013; 15(2):256-78.

Packer, J.S. et al., CLAMMS: A Scalable Algorithm for Calling Common and Rare Copy Number Variants from Exome Sequencing Data. Bioinformatics. 2016; 32(1):133-5.
Packer, J.S. et al., Supplementary Materials for CLAMMS: A Scalable Algorithm for Calling Common and Rare Copy Number Variants from Exome Sequencing Data. Bioinformatics Advance Access. 2015 (24 pages).
Peloso, G.M. et al., Association of Low-Frequency and Rare Coding-Sequence Variants with Blood Lipids and Coronary Heart Disease in 56,000 Whites and Blacks. Am J Hum Genet. 2014; 94(2):223.
Pinto, D. et al., Comprehensive Assessment of Array-Based Platforms and Calling Algorithms for Detection of Copy Number Variants. Nature Biotechnol. 2011; 29(6):512-20.
Plagnol et al. (2012) A robust model for read count data in exome sequencing experiments and implications for copy number variant calling. Bioinformatics, 28 (21), 2747-54.
Pollin, T.I. et al., A Null Mutation in Human APOC3 Confers a Favorable Plasma Lipid Profile and Apparent Cardioprotection. Science. 2008; 322(5908):1702-5.
Psaty, B.M. et al., Cohorts for Heart and Aging Research in Genomic Epidemiology (CHARGE) Consortium. Circulation: Cardiovascular Genetics. 2009; 2(1): 73-80.
Raal, F.J., Mipomersen, an Apolipoprotein B Synthesis Inhibitor, for Lowering of LDL Cholesterol Concentrations in Patients with Homozygous Familial Hypercholesterolaemia: A Randomised, Double-Blind, Placebo-Controlled Trial. Lancet. 2010; 375(9719): 998-1006.
Rahman, N., Realizing the Promise of Cancer Predisposition Genes. Nature. 2014; 505(7483): 302-8.
Reid, J.G. et al., Launching Genomics into the Cloud: Deployment of Mercury, a Next Generation Sequence Analysis Pipeline. BMC Bioinformatics. 2014; 15:30 (11 pages).
Response to Final Rejection and Request for Continued Examination (RCE) dated May 25, 2018 to the USPTO office for U.S. Appl. No. 14/714,949, filed May 18, 2015 and published as US-2016/0342733-A1 on Nov. 24, 2016 (Inventor—Jeffrey Reid) (23 pages).
Response to Non Final Rejection dated Apr. 5, 2019 to the USPTO office for U.S. Appl. No. 14/714,949, filed May 18, 2015 and published as US-2016/0342733-A1 on Nov. 24, 2016 (Inventor—Jeffrey Reid) (33 pages).
Response to Non Final dated Oct. 23, 2017 to the USPTO for U.S. Appl. No. 14/714,949, filed May 18, 2015, and published as US 2016-0342733 A1 on Nov. 24, 2016 (Applicant—Jeffrey Reid ) (30 pages).
Richards, S. et al., Standards and Guidelines for the Interpretation of Sequence Variants: A Joint Consensus Recommendation of the American College of Medical Genetics and Genomics and the Association for Molecular Pathology. Genet Med. 2015; 17(5):405-24.
Robinson, J.T., "The K-D-B-Tree: A Search Structure for large Multidimensional Dynamic Indexes", ProceedingSIGMOD '81 Proceedings of the 1981 ACM SIGMOD international conference on Management of data pp. 10-18.
Sham, P.C. and Purcell, S.M., Statistical Power and Significance Testing in Large-Scale Genetic Studies. Nature Rev Genet. 2014; 15(5):335-46.
Skre, H., Genetic and Clinical Aspects of Charcot-Marie-Tooth's Disease. Clin Genet. 1974; 6(2):98-118.
Staples, J. et al., PRIMUS: Repid Reconstruction of Pedigrees from Genome-wide Estimates of Identity by Descent. Am J Hum Genet. 2014; 95(5): 553-64.
Steinberg, S. et al., Loss-of-Function Variants in ABCA7 Confer Risk of Alzheimer's Disease. Nat Genet. 2015; 47(5):445-7.
Stenson et al. (2012) The Human Gene Mutation Database (HGMD) and its exploitation in the fields of personalized genomics and molecular evolution. Curr Protoc Bioinformatics, doi: 10.1002/0471250953.bi0113s39.
Sudmant, P.H. et al., An Integrated Map of Structural Variation in 2,504 Human Genomes. Nature. 2015;526(7571):75-81.
Sulem, P. et al., Identification of a Large Set of Rare Complete Human Knockouts. Nat Genet. 2015;47(5):448-52.
Surakka et al., The Impact of Low-Frequency and Rare Variants on Lipid Levels. Nat Genet. 2015; 47(6):589-97.

(56) References Cited

OTHER PUBLICATIONS

Szigeto, K. and J.R. Lupski, Charcot-Marie-Tooth Disease. Eur J Hum Genet. 2009; 17(6):703-10.
Tennessen, J.A. et al., Evolution and Funcitonal Impact of Rare Coding Variation from Deep Sequencing of Human Exomes. Science. 2012; 337(6090):64-9.
Teslovich, T.M. et al., Biological, Clinical and Population Relevance of 95 Loci for Blood Lipids. Nature. 2010; 466(7307): 707-13.
The 1000 Genomes Project Consortium et al., An Integrated Map of Genetic Variation from 1,092 Human Genomes. Nature. 2012; 491(7422):56-65.
The 1000 Genomes Project Consortium, A Map of Human Genome Variation from Population-Scale Sequencing. Nature. 2010; 467(7319):1061-73.
The UK10k Consortium, The UK10k Project Identifies Rare Variants in Health and Disease. Nature. 2015; 526(7571):82-90.
Thomas, G.S. et al., Mipomersen, an Apolipoprotein B Synthesis Inhibitor, Reduces Atherogenic Lipoproteins in Patients with Severe Hypercholesterolemia at High Cardiovascular Risk. J Am Coll Cardiol. 2013; 62(23): 2178-84.
Turner, D.J. et al., Gremline Rates of de Novo Meiotic Deletions and Duplications Causing Several Genomic Disorders. Nat Genet. 2008; 40(1): 90-5.
Valenzuela et al., High-throughput Engineering of the Mouse Genome Coupled with High-resolution Expression Analysis. Nat Biotechnol. 2003; 21(6): 652-9.
Valsesia, et al. "The growing importance of CNVs:new insights for detection and clinical interpretation", Front Genet. (2013), 4:92.
Van Bon, B.W. et al., Further Delineation of the 15q13 Microdeletion and Duplication Syndromes: a Clinical Spectrum Varying from Non-Pathogenicto a Severe Outcome. J Med Genet. 2009; 46(8):511-23.
Van der Sluis, S. et al., TATES: Efficient Multivariate Genotype-Phenotype Analysis for Genome-Wide Association Studies. PLoS Genetics. 2013; 9(1):e1003235 (9 pages).
Visscher, P.M. et al., Five Years of GWAS Discovery. Am J Hum Genet. 2012; 90(1): 7-24.
Wang et al. (2007). PennCNV: An integrated hidden Markov model designed for high-resolution copy number variation detection in whole-genome SNP genotyping data. Genome Res, 17 (11): 1665-1674.
Wang et al., Copy Number Variation Detection Using Next Generation Sequencing Read Counts, BMC Bioinformatics, 15: 109 (2014).
Wang, K. et al., PennCNV: An Integrated Hidden Markov Model Designed for High-Resolution Copy Number Variation Detection in Whole-Genome SNP Genotyping Data. Genome Res. 2007; 17(11): 1665-74.
Wellcome Trust Case Control Consortium, Genome-Wide Association Study of 14,000 Cases of Seven Common Diseases and 3,000 Shared Controls. Nature. 2007; 447(7145): 661-78.
Wellcome Trust Case Control Consortium, Genome-Wide Association Study of CNVs in 16,000 Cases of Eight Common Diseases and 3,000 Shared Controls. Nature. 2010; 464: 713-20.
Welty, F.K., Hypobetalipoproteinemia and Abetalipoproteinemia. Curr Opin Lipidol. 2014; 25(3): 161-8.
Wishart, D.S. et al., DrugBank: A Comprehensive Resource for in Silico Drug Discovery and Exploration. Nucleic Acids Res. 2006; 34(Database Issue): D668-72.
Wooley et al., Catalyzing Inquiry at the Interface of Computing and Biology, National Academy of Sciences/National Research Council (2005)(469 pages).
Wu, M.C. et al., Rare-Variant Association Testing for Sequencing data with the Sequence Kernet Association Test. Am J Hum Genet. 2011; 89(1): 82-93.

Yamamoto, et al. Challenges in detecting genomic copy number aberrations using next-generation sequencing data and the eXome Hidden Markov Model: a clinical exome-first diagnostic approach, Human Genome Variation vol. 3, Article No. 16025 (2016).
Yang, J. et al., GCTA: A Tool for Genome-wide Complex Trait Analysis. Am J Hum Genet. 2011; 88(1): 76-82.
Yang, Y. et al., Molecular Findings Among Patients Referred for Clinical Whole-Exome Sequencing. JAMA. 2014; 312:1870.
Ye, K. et al., Pindel: A Pattern Growth Approach to Detect Break Points of Large Deletions and Medium Sized Insertions from Paired-end Short Reads. Bioinformatics. 2009; 25(21): 2865-71.
Zare, et al. An evaluation of copy number variation detection tools for cancer using whole exome sequencing data, BMC Bioinformatics. 2017; 18: 286.
Zhang, F. et al., Copy Number Variation in Human Health, Disease, and Evolution. Annu Rev Genomics Hum Genet. 2009; 10: 451-81.
Zhao, M. et al., Computational Tools for Copy Nummber Variation (CNV) Detection Using Next-Generation Sequencing Data: Features and Perspectives. BMC Bioinformatics. 2013; 14(Suppl 11): 1-16.
Office Action dated Mar. 4, 2021 by the USPTO for U.S. Appl. No. 15/473,302, filed Mar. 29, 2017 (Applicant—Regeneron Pharmaceuticals, Inc.) (22 pages).
Office Action dated Aug. 9, 2021 by the Chinese Patent Office for CN Application No. 201680029079.8, filed on May 13, 2016 (Applicant—Regeneron Pharmaceuticals, Inc.) (4 pages).
Office Action dated Jul. 27, 2020 by the Korean Patent Office for KR Application No. 2017-7036068, filed on May 13, 2016 (Applicant—37595—(Regeneron Pharmaceuticals, Inc.) (English Translation 13 Pages).
Office Action dated Feb. 5, 2021 by the Canadian Patent Office for CA Application No. 3018186, filed on Mar. 29, 2017 (Applicant—Regeneron Pharmaceuticals, Inc.) (4 pages).
U.S. Appl. No. 14/714,949 (U.S. Pat. No. 10,395,759), filed May 18, 2015 (Aug. 27, 2019), Jeffrey Reid.
U.S. Appl. No. 62/294 669, filed Feb. 12, 2016, Evan Maxwell et al.
U.S. Appl. No. 15/431,715 (2017/0233806), filed Feb. 13, 2017 (Aug. 17, 2017), Evan Maxwell et al.
U.S. Appl. No. 62/314,684, filed Mar. 29, 2016, Jeffrey Reid et al.
U.S. Appl. No. 62/362,660, filed Jul. 15, 2016, Jeffrey Reid et al.
U.S. Appl. No. 62/4404,912, filed Oct. 6, 2016, Jeffrey Reid et al.
U.S. Appl. No. 62/467,547, filed Mar. 6, 2017, Jeffrey Reid et al.
U.S. Appl. No. 15/473,302 (2017/0286594), filed Mar. 29, 2017 (Oct. 5, 2017), Jeffrey Reid et al.
Office Action dated Nov. 26, 2019 by the Japanese Patent Office for JP Application No. 2018-542281, filed on Feb. 13, 2017 and published as JP 2019-512122 on May 9, 2019 (Applicant—37595—(Regeneron Pharmaceuticals, Inc.) (Original—3 Pages// Translation—3 Pages).
Non Final Rejection dated Dec. 12, 2019 by the USPTO for U.S. Appl. No. 15/431,715, filed Feb. 13, 2017 and published as US-2017/0233806-A1 on Aug. 17, 2017(Inventor—Evan Maxwell) (10 Pages).
Office Action dated Jan. 21, 2020 by the Japanese Patent Office for JP Application No. 2017-559843, filed on May 13, 2016 and published as JP 2018-523198 on Aug. 16, 2018 (Applicant—Regeneron Pharmaceuticals, Inc.) (Original—4 Pages// Translation—3 Pages).
Office Action dated Feb. 3, 2020 by the Russian Patent Office for RU Application No. 2017143983, filed on May 13, 2016 (Applicant—Regeneron Pharmaceuticals, Inc.) (4 Pages).
Office Action dated Sep. 24, 2021 by the Indian Patent Office for IN Application No. 201747044337, filed on May 13, 2016 (Applicant—Regeneron Pharmaceuticals, Inc.) (6 pages).
Office Action dated Dec. 15, 2020 by the Chinese Patent Office for CN Application No. 201680029079.8, filed on May 13, 2016 (Applicant—Regeneron Pharmaceuticals, Inc.) (8 pages).

* cited by examiner

FIG. 9

| Algorithm | # Calls | | | Call Statistics (%) | | |
|---|---|---|---|---|---|---|
| | Total | Common | Rare | Consistent | Transmitted | Inherited |
| CLAMMS | 253 | 205 | 48 | 93.7 | 61.1 | 97.8 |
| XHMM | 86 | 25 | 61 | 38.5 | 10.6 | 23.3 |
| CoNIFER | 40 | 14 | 26 | 68.1 | 25.5 | 75.6 |
| CANOES | 26 | 15 | 11 | 92.6 | 0.0 | 0.0 |
| ExomeDepth | 279 | 202 | 77 | 68.9 | 30.6 | 64.7 |

FIG. 10

| Metric | Algorithm | Any Overlap | 33% Overlap | 50% Overlap |
|---|---|---|---|---|
| Precision | CLAMMS | 78.4 | 71.9 | 67.2 |
| | XHMM (Q30) | 66.4 | 60.2 | 55.4 |
| | XHMM (Q60) | 71.2 | 64.5 | 59.2 |
| Recall | CLAMMS | 65.4 | 49.7 | 41.9 |
| | XHMM (Q30) | 64.1 | 51.7 | 44.3 |
| | XHMM (Q60) | 59.9 | 49.7 | 42.5 |
| F-score | CLAMMS | 71.3 | 58.8 | 51.6 |
| | XHMM (Q30) | 65.2 | 55.6 | 49.2 |
| | XHMM (Q60) | 65.1 | 56.1 | 49.5 |

FIG.11

| CNV | Size | Type | Gene† | Validated? |
|---|---|---|---|---|
| chr1:230371759-230415205 | 43,446 | DUP | *GALNT2* | YES |
| chr10:113913307-114136207 | 222,900 | DUP | *GPAM* | YES |
| chr11:104815479-105009807 | 194,328 | DUP | *CARD16* | YES |
| chr12:21007961-21392124 | 384,163 | DEL | *SLCO1B1* | YES |
| chr13:114514707-114538608 | 23,901 | DUP | *GAS6* | YES |
| chr14:74753163-74991929 | 238,766 | DUP | *NPC2* | YES |
| chr15:85147158-85681135 | 533,977 | DEL | *NMB* | YES |
| chr16:21152620-21289573 | 136,953 | DUP | *CRYM* | YES |
| chr17:12798256-12920439 | 122,183 | DUP | *ELAC2* | YES |
| chr18:2544651-2707644 | 162,993 | DUP | *SMCHD1* | YES |
| chr18:64176231-64239442 | 63,211 | DEL | *CDH19* | YES |
| chr19:52271911-52588055 | 316,144 | DUP | *FPR3* | YES |
| chr2:55910919-55920959 | 10,040 | DUP | *PNPT1* | YES |
| chr3:124390506-124492760 | 102,254 | DUP | *UMPS* | YES |
| chr4:10560030-10567775 | 26,550 | DEL | *CLNK* | YES |
| chr7:82505086-82505804 | 718 | DEL | *PCLO* | NO |
| chr7:121738503-121773781 | 35,278 | DEL | *AASS* | YES |
| chrX:53560269-53622364 | 62,095 | DUP | *HUWE1* | YES |
| chrX:105137824-105571052 | 433,228 | DUP | *SERPINA7* | YES |
| chrX:120181538-120183935 | 2307 | DEL | *GLUD2* | YES |

† gene that led CNV to be selected (because of a disease association in HGMD)

FIG. 12

| CNV Locus | Size | Type | Gene[†] | # CNV[‡] | False + | False − |
|---|---|---|---|---|---|---|
| chr1:1634014-1663063 | 29,049 | Both | CDK11A | 27 | 0 | 5 |
| chr1:16370087-16390132 | 19,145 | DUP | CLCNKB | NA* | NA | NA |
| chr1:152573207-152586575 | 13,368 | DEL | LCE3B | 130 | 0 | 38 |
| chr1:206317576-206331229 | 13,653 | DEL | CTSE | 10 | 0 | 0 |
| chr10:27687222-27703180 | 15,958 | DEL | PTCHD3 | 10 | 0 | 0 |
| chr10:135340899-135379034 | 38,135 | DUP | SYCE1 | 13 | 0 | 1 |
| chr11:8959162-8959721 | 559 | DEL | ASCL3 | 8 | 0 | 1 |
| chr11:134151918-134214350 | 62,432 | Both | GLB1L3 | NA* | NA | NA |
| chr19:46623586-46627907 | 4,321 | DEL | IGFL3 | 10 | 0 | 1 |
| chr19:54801926-54804222 | 2,296 | DEL | LILRA3 | 69 | 0 | 0 |
| chr2:110881367-110962546 | 81,179 | Both | NPHP1 | 7 | 0 | 0 |
| chr21:37510122-37618976 | 108,854 | DUP | CBR3 | 8 | 0 | 0 |
| chr22:24373137-24384232 | 11,095 | DEL | GSTT1 | 111 | 0 | 14 |
| chr2:241627221-241710522 | 83,301 | DUP | KIF1A | 6 | 0 | 0 |
| chr3:151531950-151545961 | 14,011 | DEL | AADAC | 11 | 0 | 1 |
| chr4:3446037-3478270 | 32,233 | DEL | HGFAC | 6 | 0 | 0 |
| chr4:69403342-69434203 | 30,861 | DEL | UGT2B17 | 100 | 0 | 1 |
| chr5:138651764-138658657 | 6,893 | DUP | MATR3 | NA* | NA | NA |
| chr7:142829209-142881529 | 52,320 | DEL | PIP | 9 | 0 | 0 |
| chr9:215201-464220 | 249,019 | DUP | DOCK8 | 6 | 1 | 0 |

\* The variance of the TaqMan data for these loci was too high to determine copy number state
† gene that led CNV to be selected (because of a disease association in HGMD)
‡ Not representative of CNV allele frequency. The 165 samples tested for common CNV loci

FIG. 15

METHODS AND SYSTEMS FOR COPY NUMBER VARIANT DETECTION

CROSS REFERENCE TO RELATED PATENT APPLICATION

This application is a continuation of U.S. patent application Ser. No. 14/714,949, filed May 18, 2015, which is herein incorporated by reference in its entirety.

BACKGROUND

Genomic sequencing is an effective tool to discover the genetic basis of Mendelian disorders. Analysis of genomic sequences has revealed the existence of copy number variants (CNVs) (e.g., the number of copies of a particular gene in the genotype of an individual). CNVs may have important roles in human disease and/or drug response. However, calling CNVs from genomic sequence data (e.g., exome sequence data) is challenging. Current solutions detect CNVs from human sequencing read depth, but are not been well-suited for large population studies on the order of tens or hundreds of thousands of exomes. Their limitations, among others, include being difficult to integrate into automated variant calling pipelines and being ill-suited for detecting common variants. These and other shortcomings are addressed in the present disclosure.

SUMMARY

It is to be understood that both the following general description and the following detailed description are exemplary and explanatory only and are not restrictive. Methods and systems for determining copy number variants are disclosed. An example method can comprise applying a sample grouping technique to select reference coverage data, normalizing sample coverage data comprising a plurality of genomic regions, and fitting a mixture model to the normalized sample coverage data based on the selected reference coverage data. An example method can comprise identifying one or more copy number variants (CNVs) according to a Hidden Markov Model (HMM) based on the normalized sample coverage data and the fitted mixture model. An example method can comprise outputting the one or more copy number variants.

In an aspect, another example method can comprise providing sample coverage data comprising a plurality of genomic regions and receiving an indication of reference coverage data. The reference coverage data can be selected based on a sample grouping technique. The method can comprise selecting one or more filters to apply to the sample coverage data to normalize the sample coverage data and requesting fitting of a mixture model to the normalized sample coverage data based on the reference coverage data. The method can comprise requesting identifying one or more copy number variants according to a Hidden Markov Model (HMM) based on the normalized sample coverage data and the fitted mixture model. The method can further comprise receiving an indication of the one or more copy number variants.

In an aspect, another example method can comprise receiving sample coverage data comprising a plurality of genomic regions, retrieving one or more metrics for the sample coverage data, applying a sample grouping technique to the sample coverage data and reference coverage data to select a subset of the reference coverage data, normalizing the sample coverage data comprising the plurality of genomic regions, and fitting a mixture model to the normalized sample coverage data based on the subset of the reference coverage data. The method can comprise identifying one or more copy number variants according to a Hidden Markov Model (HMM) based on the normalized sample coverage data and the fitted mixture model. The method can comprise outputting the one or more copy number variants.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 9 is a table illustrating performance metrics for CNV calls on the CEPH pedigree;

FIG. 10 shows CLAMMS and XHMM CNV calls compared to PennCNV gold-standard;

FIG. 11 shows a table illustrating Rare CNV TaqMan Validations;

FIG. 12 shows a table illustrating common CNV TaqMan Validations;

FIG. 15 is an example output.

DETAILED DESCRIPTION

Figure 1:
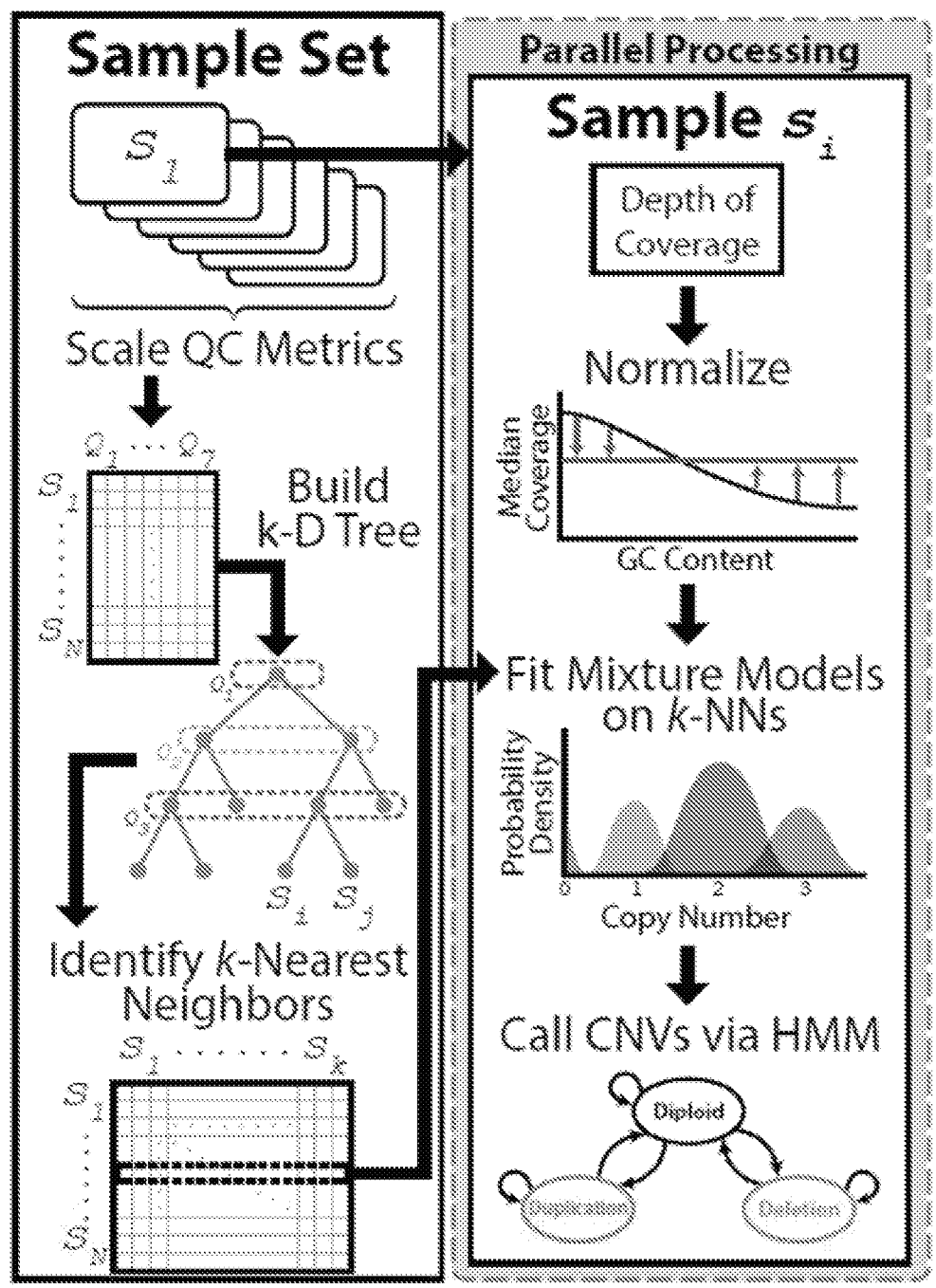
FIG. 1 is flowchart illustrating an example CNV-calling pipeline.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present methods and system which will be limited only by the appended claims.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems are directed to CNV detection (e.g., identification, prediction, estimation). Some aspects of the present methods and systems can be referred to as "Copy number estimation using Lattice-aligned Mixture Models (CLAMMS)." Detecting copy number variants with whole exome sequencing (WES) data can be challenging because CNV breakpoints are likely to fall outside of the exome. The present methods and systems can utilize read depths within the CNV. Such read depths can be linearly correlated to copy number state. However, depth-of-coverage can be subject to both systematic biases (e.g., often related to sequence GC-content) and stochastic volatility (e.g., which is exacerbated by variation in input DNA quality). The present methods and systems can normalize coverage data to correct for systematic biases and characterize the expected coverage profile given diploid copy number so that true CNVs can be distinguished from noise. Such normalization can comprise, for example, comparing each sample's coverage data to data from a "reference panel" (e.g., reference coverage data) of similarly-sequenced samples. Variability in sample preparation and sequencing procedures can result in additional coverage biases that are commonly referred to as "batch effects."

In an aspect, the present method and systems can identify CNVs based on the use of both mixture models and Hidden Markov Models (HMM). For example, mixture models can be fit based on reference coverage data determined using a sample grouping algorithm, such as k-nearest neighbor algorithm. Information from the mixture models can be input into an HMM for identification of CNVs.

FIG. 1 is flowchart illustrating an example CNV-calling pipeline. A reference panel of coverage data (e.g., reference coverage data comprising one or more genomic capture regions) can be selected for each sample (e.g., sample coverage data comprising one or more genomic capture regions) based on a plurality of metrics (e.g., sequencing Quality Control (QC) metrics) using a sample grouping technique. The sample grouping technique can comprise a technique (e.g., algorithm) for grouping samples by similarity. Examples of sample grouping techniques that can be used include, but are not limited to, a decision tree, a support-vector machine, a k-nearest neighbors (knn) algorithm, a Naïve Bayes algorithm, a CART (Classification and Regression Trees) algorithm, and/or the like. For example, a kNN algorithm can comprise generating a k-d tree data structure. The reference coverage data can be selected by inserting the sample coverage data (e.g., or metrics associated with the sample coverage data) into the k-d tree structure and identifying a predetermined number of nearest neighbors (e.g., 10, 100, 1000, 10000, etc. . . . ). After selecting reference coverage data, samples can be processed in parallel. Sample-level analysis (right panel) includes normalizing coverage, fitting coverage distributions with a mixture model, and generating calls from an HMM.

In an aspect, an example implementation of the present methods and systems is disclosed in FIG. 1. As shown in the left panel, reference coverage data (e.g., pulled from a sample set) can be used as part of the sample grouping technique. Though a k-nearest neighbor algorithm that utilizes a k-d tree is used to illustrate the sample grouping technique, it should be appreciated that other sample grouping techniques can be applied (e.g., any appropriate clustering, grouping, and/or classification algorithm). The k-d tree can comprise a multidimensional search tree for points in k dimensional space. For example, a plurality of metrics of the reference coverage data can be used by the sample grouping technique. For example, the plurality of metrics of the reference coverage data can be used to build the k-d tree. The plurality of metrics can comprise, for example, sequencing quality control (QC) metrics, sample metadata, ancestry-based values, sequence-similarity scores, and/or any metric that captures sample-level variability. For example, in the case of sequencing QC metrics, seven QC metrics can be used. As an illustration, the sequencing QC metrics can comprise GCDROPOUT, ATDROPOUT, MEANINSERTSIZE, ONBAITVSSELECTED, PCTPFUQREADS, PCTTARGETBASES10X, PCTTARGETBASES50X, and/or the like. The sequencing QC metrics can be scaled (e.g., by applying a linear transform) and processed to build the k-d tree.

A plurality of metrics (e.g., sequencing QC metrics) for sample coverage data can also be scaled and inserted into the k-d tree. The k-d tree can then be used to perform a nearest neighbor search to identify the nearest neighbors to the sample coverage data. Any number of nearest neighbors in the reference coverage data can be identified (e.g., 10, 100, 1000, 10000, etc. . . . ). The desired number of nearest neighbors can be used to form selected reference coverage data (e.g., a subset of the reference coverage data). The present methods and systems can address data heterogeneity by selecting custom reference coverage data for each sample. By way of example, a distance metric between samples (e.g., reference coverage data) can be defined based on the seven sequencing QC metrics described above. For example, the sequencing QC metrics can be determined, selected, received, and/or the like from a sequencing tool, such as Picard. Each newly sequenced sample can be added to a k-d tree in this metric space. CNVs can be called using selected reference coverage data comprising the individual sample's k (e.g., 100) nearest neighbors. The k-nearest neighbors can be found using any nearest neighbors algorithm, such as a k-d tree algorithm or other sample grouping technique.

As shown in the right panel, sample coverage data (e.g., sample i) can be selected from a sample set. The sample coverage data can be normalized to correct for GC-amplification bias and overall average depth-of-coverage. In another aspect, sample coverage data can be filtered. For example, sample coverage data can be filtered based on a level of GC content, based on a mappability score, based on a measure of central tendency of read coverage, based on occurrence of a calling window in a multi-copy duplication exome capture region, combinations thereof and the like. For example, read depths in low-mappability regions may not accurately represent the sequence dosage in the genome.

Once the sample coverage data has been normalized, the selected reference coverage data (nearest neighbors) can be used to fit a finite mixture model for one or more (or each) genomic (e.g., exome) capture regions in the sample coverage data. A finite mixture model can comprise a combination of two or more probability density functions. Finite mixture models can comprise one or more components, such as: N random variables corresponding to observations, each assumed to be distributed according to a mixture of K components, with each component belonging to the same parametric family of distributions but with different parameters; N corresponding random latent variables specifying the identity of the component of the mixture model of each observation, each distributed according to a K-dimensional categorical distribution; a set of K mixture weights, each of which is a probability (a real number between 0 and 1 inclusive), all of which sum to 1; a set of K parameters, each specifying the parameter of the corresponding component of the mixture model. In some aspects, a parameter can comprise a set of parameters. In the present methods and systems, each component of the mixture model can model the expected distribution of coverage across samples for a particular integer copy number state. Accommodations can be made to handle homozygous deletions and sex chromosomes.

In an aspect, an expectation-maximization (EM) algorithm can be used to fit the finite mixture model. The EM algorithm is a general method for finding maximum likelihood estimates when there are missing values or latent variables. The EM algorithm can be an iterative algorithm. The iterations can alternate between performing an expectation (E) step, which can generate a function for the expectation of the log-likelihood evaluated using the current estimate for the parameters, and a maximization (M) step, which can compute parameters maximizing the expected log-likelihood found on the E step. These parameter-estimates can then be used to determine the distribution of the latent variables in the next E step.

In an aspect, CNVs can be called for the sample coverage data using a Hidden Markov Model (HMM). For example, the individual sample's normalized coverage values for each region can be the input sequence to the HMM. Emission probabilities of the HMM can be based on the trained (e.g., fit, adapted) mixture models. Transition probabilities of the HMM can be similar to those used by other models, such as XHMM, incorporated herein by reference. Mixture models allow for copy number polymorphic loci to be handled naturally, while the HMM incorporates the prior expectation that nearby anomalous signals are more likely to be part of a single CNV than multiple small CNVs. The present methods and systems can integrate mixture models and HMMs into a single probabilistic model.

Figure 2:
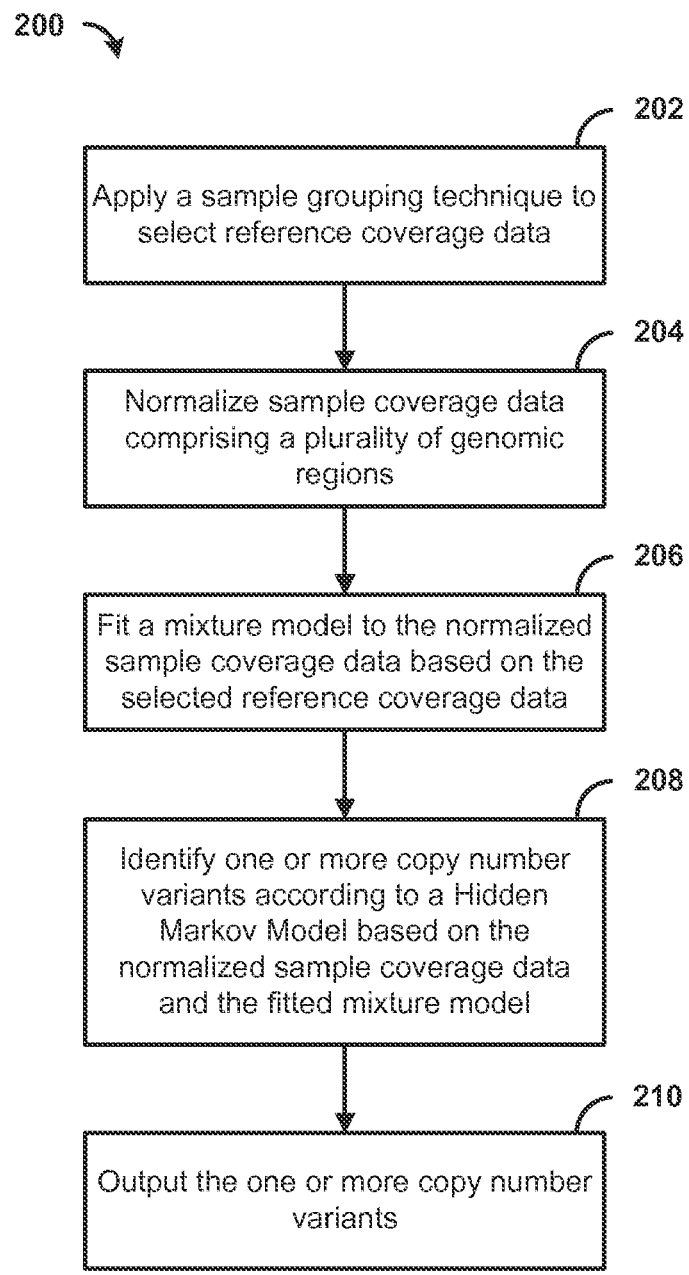
FIG. 2 is a flowchart illustrating an example method for determining copy number variants.

FIG. 2 is a flowchart illustrating an example method 200 for determining copy number variants. In an aspect, the present method and system can be configured for analyzing sample coverage data comprising a plurality of genomic regions to detect CNVs. At step 202, a sample grouping technique can be applied to select reference coverage data. For example, the sample grouping technique can comprise a technique (e.g., algorithm) for grouping samples by similarity. Applying a sample grouping technique to select reference coverage data can comprise receiving a plurality of metrics for the sample coverage data. A distance metric between the sample coverage data and the reference coverage data can be defined based on the plurality of metrics. The reference coverage data can be selected (e.g., for each sample) based on the distance metric. The sample grouping technique can comprise a grouping algorithm, clustering algorithm, classification algorithm, and/or the like. For example, the sample grouping technique can comprise a decision tree, a support-vector machine, a k-Nearest Neighbors (knn) algorithm, a Naïve Bayes algorithm, a CART (Classification and Regression Trees) algorithm, and/or the like. For example, applying the sample grouping technique to select reference coverage data the method can comprise scaling a plurality of metrics associated with the reference coverage data, generating a k-d tree based on the scaled plurality of metrics associated with the reference coverage data, scaling a plurality of metrics associated with the sample coverage data, adding the sample coverage data to the k-d tree based on the scaled plurality of metrics associated with the sample coverage data, identifying a predetermined number of nearest neighbors to the sample coverage data as the selected reference coverage data, and/or the like.

Application of the sample grouping technique to select reference coverage data is described in further detail as follows. Systematic coverage biases that arise due to variability in sequencing conditions are commonly referred to as "batch effects." In an aspect, the present methods and systems can be configured to use a custom reference panel (e.g., selected reference coverage data) approach to correct for batch effects. For example, instead of comparing sample coverage data based on the sample's coverage profiles—a high-dimensional space—the present methods and systems can be configured to consider a low-dimensional metric space based on sequencing quality control (QC) metrics. For example, the sequencing QC metrics can comprise seven sequencing QC metrics. The sequencing QC metrics can comprise sequencing QC metrics from a sequencing tool, such as Picard. Working in this low-dimensional space allows for improved scalability. For example, samples can be indexed ahead-of-time (e.g., using any appropriate indexing and/or search algorithm). As a further example, samples can be indexed ahead-of-time using a k-nearest neighbor algorithm. For example, the k-nearest neighbor algorithm can use k-d tree structure that allows for fast nearest-neighbor queries and uses a minimal amount of RAM.

As an illustration, an example variant-calling pipeline can be configured to proceed as follows:
1. Query a laboratory information management system to retrieve seven Picard sequencing quality control metrics for each sample: GCDROPOUT, ATDROPOUT, MEANINSERTSIZE, ONBAITVSSELECTED, PCTPFUQREADS, PCTTARGETBASES10X, and PCTTARGETBASES50X.
2. Insert each sample's QC-metric vector k-d tree data structure, after applying a linear transform to scale each metric into the range [0, 1] (e.g., scaled value=[raw value−min]/[max−min])
3. In parallel, for each sample:
   (a) Compute depth-of-coverage from the BAM file using samtools and run CLAMMS' within-sample normalization step.
   (b) Train CLAMMS models using the sample's 100 nearest neighbors in the k-d tree.
   (c) Call CNVs using these models.

In an aspect, larger values of k can decrease variance in the statistical inference of the mixture model parameters but increase bias. A default k value can be selected according to specific applications. In some scenarios, a default value k=100 can provide the best bias-variance trade-off. The pipeline can be extended to run via a network (e.g., web interface) if the k-d tree is stored in a database. In some scenarios, such as small-scale studies, the present methods and systems can also be used without having to compute QC metrics. For example, samples can be manually assigned to batches based on a PCA plot of a sample-by-exon coverage matrix. A separate set of models can be trained for each batch and used to call CNVs for samples in that batch.

In an aspect, the present methods and systems can divide the plurality of genomic regions of the sample coverage data into one or more calling windows (e.g., a plurality of calling windows). For example, the present methods and systems can divide genomic (e.g., exome) capture regions into equally sized calling windows. For example, genomic capture regions that are greater than or equal to 1000 bp long can be divided into equally-sized 500-1000 base pair (bp) calling windows. The present methods and systems can be configured to divide genomic regions into calling windows such that CNVs that partially overlap long exons can be detection. Examples of genes with extraordinarily long exons include AHNAK, TTN, and several Mucins. In an aspect, only genomic regions of the plurality of genomic regions larger than a predetermined size may be divided, for example, larger than 999 bases. It should be noted that any other appropriate number of bases can be used.

Figure 3:
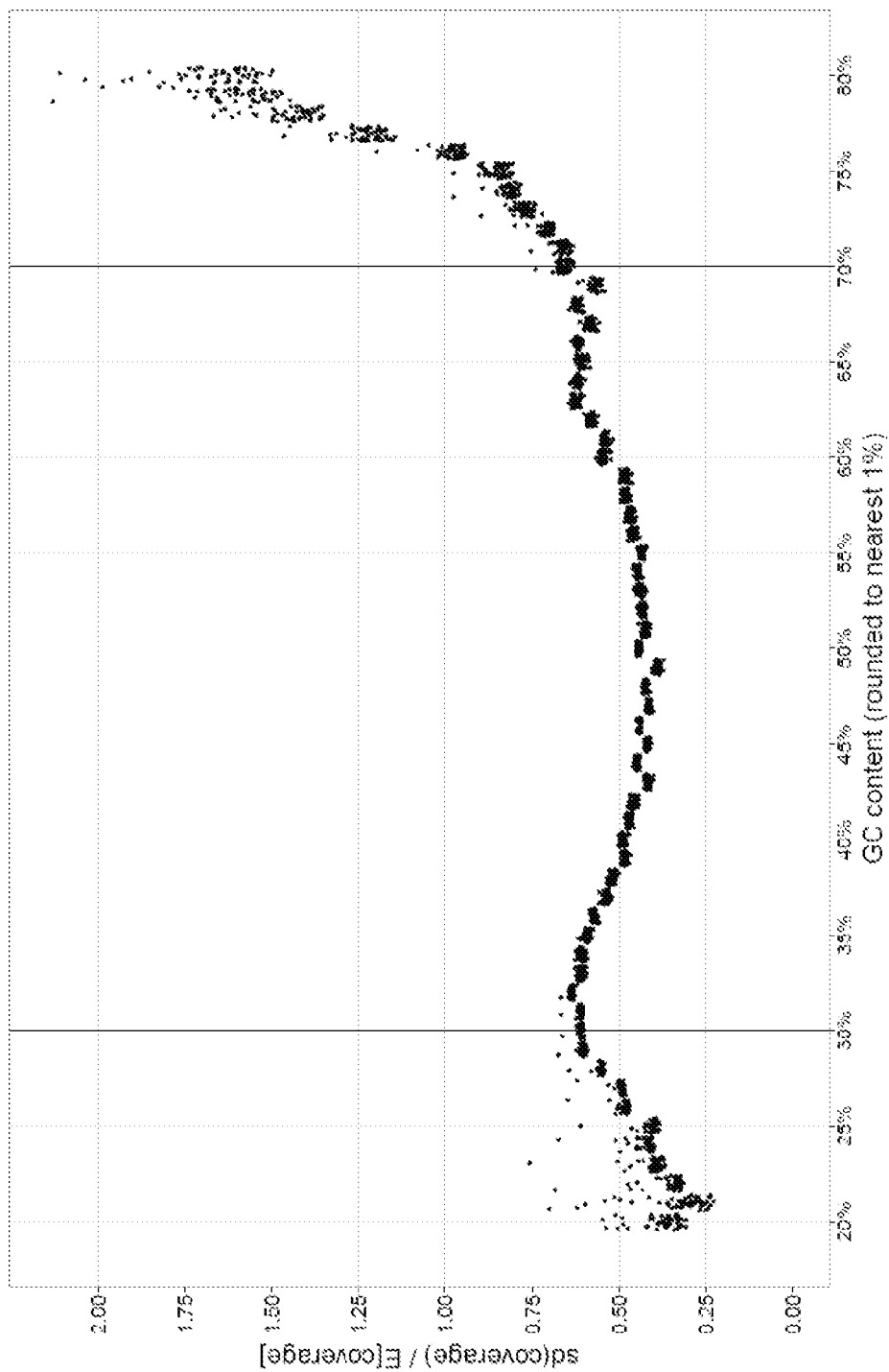
FIG. 3 shows a graph illustrating the relationship of GC content and coverage.

In an aspect, the methods and systems can optionally comprise filtering the sample coverage data. Filtering can be accomplished prior to step 202, during step 202, and/or during other steps of the method 200. Filtering the sample coverage data can comprise filtering the one or more calling windows based on a level of guanine-cytosine (GC) content. Filtering the one or more calling windows based on a level of GC content can comprise excluding a calling window of the one or more calling windows if the level of GC content of the calling window is outside a predetermined range. In an aspect, the present methods and systems can filter windows with extreme guanine-cytosine content (GC) content. GC-amplification bias can be corrected when the bias is mostly consistent for any particular level of GC content. At very low or high GC content, however, the stochastic coverage volatility may increase dramatically, making it difficult to normalize effectively. Accordingly, the present methods and systems can filter windows where the GC-fraction is outside of a configurable (e.g., or predefined) range or threshold. As an illustration, the configurable range can comprise [0.3, 0.7], as shown in FIG. 3. It should be appreciated, however, that other ranges (e.g., thresholds) can be utilized as appropriate.

As a further explanation of filtering based on GC content, FIG. 3 shows a graph illustrating the relationship of GC content and coverage. For example, the coefficient of variation (e.g., standard deviation divided by mean) of coverage is shown on the y-axis and GC content is shown in the x-axis. The graph shows 50 samples (e.g., points jittered for visibility). Above a default upper-limit (e.g., GC=0.7) of the configurable range, coverage variance can be very high relative to the mean, making coverage-based CNV calls unreliable. Below a default lower-limit (e.g., GC content=0.3) of the configurable range, additional problems arise. For example, the variance of coverage itself can be highly variable between samples. This variance makes it difficult to accurately estimate the expected variance of coverage for a particular sample at a particular window, as each reference panel sample's coverage value is an observation from a different distribution.

In an aspect, the GC content of the full DNA fragment, not only the sequenced read, can influence fragment count. Accordingly, when computing GC-fractions, windows can be symmetrically extended to be at least slightly longer than the average fragment size. The average fragment size can be another configurable parameter of CLAMMS. Average fragment size can default to 200 bp, or other appropriate values may be used.

Filtering the sample coverage data can comprise filtering the one or more calling windows based on a mappability score of a genomic region of the plurality of genomic regions. For example, the present methods and systems can filter calling windows where the mean mappability score for k-mers starting at each base in the window (default k=75) is less than 0.75. Filtering the one or more calling windows based on a mappability score can comprise determining a mappability score for each genomic region of the plurality of genomic regions and excluding a calling window of the one or more calling windows that contains the genomic region of the plurality of genomic regions if the mappability score of the genomic region of the plurality of genomic regions is below a predetermined threshold. Determining a mappability score for each genomic region of the plurality of genomic regions can comprise determining an average of an inverse reference-genome frequency of k-mers whose first base overlaps the genomic region of the plurality of genomic regions.

In another aspect, filtering the sample coverage data can comprise filtering the one or more calling windows based on a measure of central tendency of read coverage. Filtering the one or more calling windows based on a measure of central tendency of read coverage can comprise excluding a calling window of the one or more calling windows if the calling window of the one or more calling windows comprises a measure of central tendency of read coverage less than an expected coverage value for calling windows with similar GC content. For example, the present methods and systems can filter windows where the median and/or mean coverage across samples is less than 10% of the expectation for windows with similar GC content.

In another aspect, filtering the sample coverage data can comprise filtering the one or more calling windows based on occurrence of a calling window in a multi-copy duplication genomic region. Filtering the one or more calling windows based on occurrence of a calling window in a multi-copy duplication genomic region can comprise excluding a calling window of the one or more calling windows if the calling window of the one or more calling windows occurs within a region where multi-copy duplications are known to be present. As an illustration, a portion (e.g., 12% using the defaults above) of exome capture regions can be excluded from the calling process using these filters.

Returning to FIG. 2, at step 204, sample coverage data can be normalized. The sample coverage data can comprise a plurality of genomic regions. The present methods and systems can normalize the sample coverage data for each individual sample to correct for GC-bias and overall average depth-of-coverage. Normalizing sample coverage data can comprise determining raw coverage for a calling window w, determining a median coverage for the sample coverage data across the one or more calling windows conditional on a GC-fraction of the calling window w, and dividing the raw coverage by the median coverage, resulting in the normalized sample coverage data. Determining a median coverage for the sample coverage data across the plurality of windows conditional on a GC-fraction of the calling window w can comprise binning the one or more calling windows by GC-fraction, resulting in a plurality of bins, determining a median coverage for each bin of the plurality of bins, and/or determining a normalizing factor for each distinct possible GC-fraction using a linear interpolation between the median coverage for two bins nearest to the calling window w.

Normalization of sample coverage data is described in more detail as follows. For example, a conditional median can be determined (e.g., computed, calculated) by binning all windows for a sample by GC fraction (e.g., [0.300, 0.310], [0.315, 0.325], etc.). For example, a plurality of bins can be determined based on GC fraction values. One or more (or each) of the bins of the plurality of bins can be determined by dividing (e.g., equally) the total GC fraction value range based on one or more incremental values (e.g., 0.01). The median coverage for each bin can be determined (e.g., calculated, computed). The normalizing factor for a given GC fraction can be determined (e.g., calculated, computed). For example, the normalizing factor for a given GC fraction can be determined by using a linear interpolation between the median coverage for the two bins nearest to bin at issue. In an aspect, the binning resolution (e.g., size of incremental values) can be configurable. An example, default resolution can be determined (e.g., selected) that balances fine-grained binnings with the need to provide each bin with a sufficient sample size for estimation.

Figure 4:
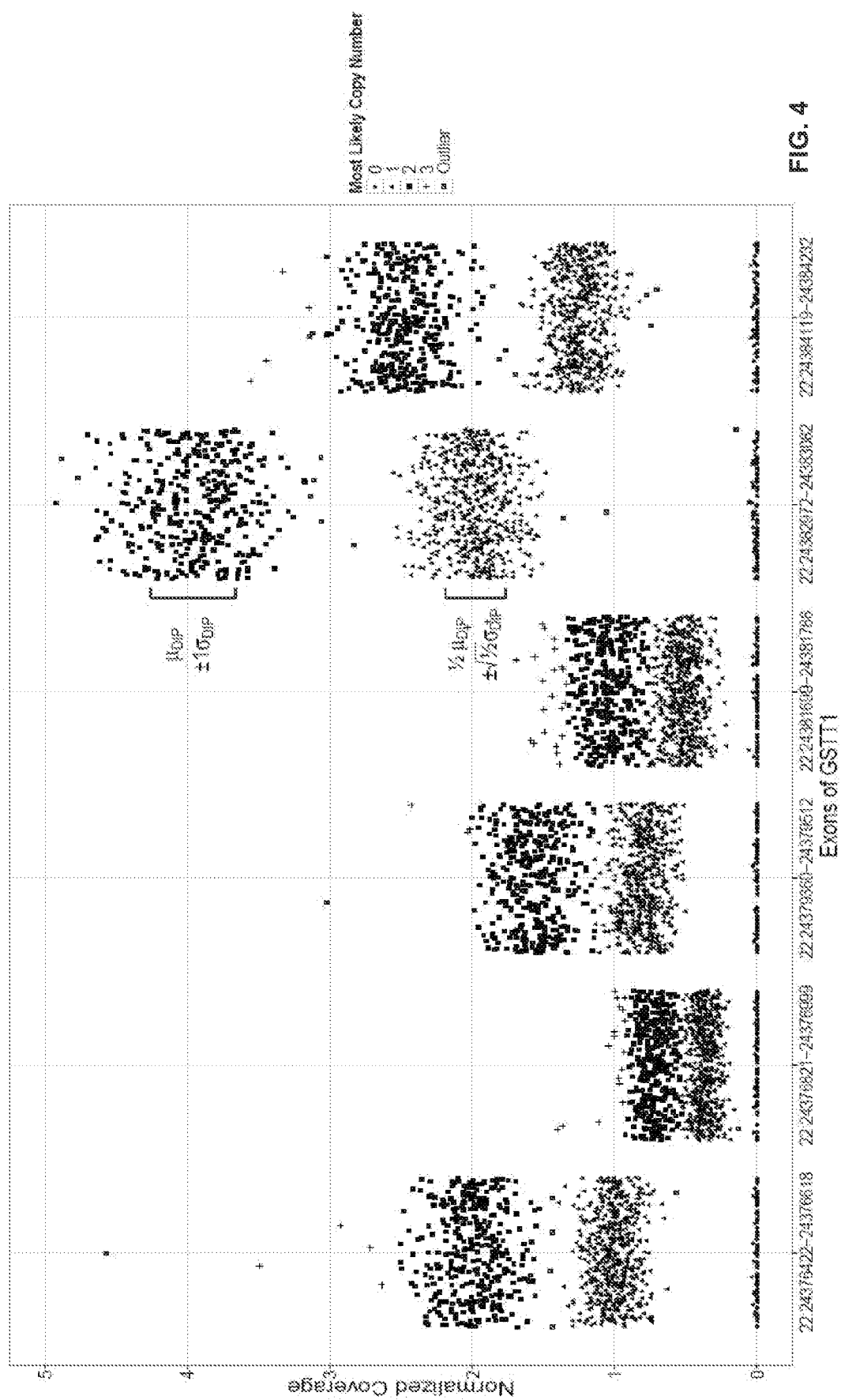
FIG. 4 is a graph illustrating normalized coverage of various exons.

FIG. 4 is a graph illustrating normalized coverage of various exons. The graph shows mixture models fit to the observed coverage distributions for exons of the gene GSTT1 (e.g., after within-sample normalization has been applied). Each point (e.g., jittered for visibility) shows a sample's normalized coverage for an exon. The shading of the plot points indicates the most likely copy number given the model and opacity proportional to the likelihood ratio between the most- and second-most-likely copy numbers if the exon were to be treated independently of its neighbors.

Returning to FIG. 2, at step 206, a mixture model can be fit (e.g., trained, modified, adapted) to the normalized sample coverage data based on the selected reference coverage data. For example, the mixture model can be trained according to the selected reference coverage data. Fitting the mixture model to the normalized sample coverage data based on the selected reference coverage data can comprise determining a plurality of mixture models (e.g., one for each of the plurality of genomic regions). One or more (or each) component of the plurality of mixture models can comprise a corresponding probability distribution. The probability distribution can represent an expected normalized coverage conditional on a particular copy number. The plurality of mixture models can be fit to the normalized sample coverage data using an expectation-maximization algorithm. For example, the plurality of mixture models can be fit to the normalized sample coverage data using an expectation-maximization algorithm to determine a likelihood for each copy number at each of the one or more calling windows. The selected reference coverage data can be input to the expectation-maximization algorithm.

As a further explanation, the present methods and systems can use mixture models to characterize the expected normalized coverage distribution at each calling window. The expected coverage distribution can be conditional on copy number state. These mixture models can be fit by using a fitting algorithm. For example the mixture models can be fit by identifying the model parameters that best match the shape of the data distribution. In an aspect, the fitting algorithm can comprise an optimization method for estimating the mixture model parameters, such as EM. Alternatively, an unsupervised clustering or sampling algorithm could be used to identify distinct copy number states and/or model the distribution of coverage data over copy number states.

For example, the fitting algorithm can comprise an expectation-maximization algorithm (EM algorithm) with input data from a reference panel of samples (e.g., reference coverage data). In an aspect, the EM algorithm can comprise an optimization algorithm for fitting hidden (e.g., latent) model parameters. In some implementations, the fitting algorithm can comprise the use of gradient descent, Newton-Raphson, and/or the like algorithms. The components of the mixture model can correspond to the copy numbers 0, 1, 2, and 3. In some implementations, copy numbers greater than 3 can be ignored. For example, coverage that could be explained by copy number greater than 3 may be the result of stochastic GC-related bias.

In an aspect, one or more of the components of the mixture model corresponding to non-zero copy numbers can be defined to follow a Gaussian distribution. For example, the Gaussian distribution can be of the form:

$$\frac{1}{sqrt(2\pi\sigma^2)}e^{-\frac{(x-\mu)^2}{2\sigma^2}}$$

where $\mu$ indicates a mean and $\sigma$ indicates a variance or standard deviation. The Gaussian distribution for a diploid copy can comprise at least two free parameters: $\mu_{DIP}$ (e.g., the mean of the mixture component corresponding to diploid copy) and $\sigma_{DIP}$ (e.g., standard deviation of the mixture component corresponding to diploid copy). For each non-diploid copy number k, the mean can be constrained to equal $(k/2)*\mu_{DIP}$ (e.g., hence the term "lattice-aligned" in the CLAMMS acronym). The standard deviation for haploid samples, $\sigma_{HAP}$, can be set equal to $\sqrt{0.5}*\sigma_{DIP}$. Despite the Gaussian approximations, coverage conditional on a particular copy number can be Poisson-distributed with variance being equal to the mean. The standard deviation parameters for components corresponding to copy numbers greater than 2 can be set to be equal to $\sigma_{DIP}$. This configuration can avoid increasing the rate of false-positive duplications. The constraints imposed on the parameters of the non-diploid components can configure the model to avoid overfitting the training data.

In an aspect, the fitting algorithm can be configured to account for mismapped reads corresponding to deleted regions. For example, one or more of the components of the mixed model can be defined as an exponential distribution. Homozygous deletions (e.g., copy number 0) can show zero coverage, but mismapped reads can give a small level of coverage even in truly deleted regions. Accordingly, the component corresponding to copy number 0 can be defined as an exponential distribution. The exponential distribution can comprise rate parameter $\lambda$. For example, an exponential distribution can be of the following form: $\lambda e^{-\lambda x}$. The exponential distribution can be configured with a mean (e.g., $1/\lambda$) initially equal to 6.25% of $\mu_{DIP}$ or other appropriate ratio. As a further example, the mean of this component can be constrained to be no greater than this initial value. If there are no mismapping issues with the region, iterations of the fitting algorithm can drive the mean to 0 (e.g., $\lambda \to \infty$). To address this issue, if the mean drops below 0.1% of $\mu_{DIP}$, the fitting algorithm can replace the exponential distribution with a point mass at 0.

In summary, the mixture model can be configured with one or more of the following parameters: $\mu_{DIP}$ and $\sigma_{DIP}$; $\lambda$, the rate of the exponential component (e.g., copy number 0), and a flag indicating if the exponential has been replaced by a point mass.

In an aspect, the fitting algorithm can be configured to iteratively converge on a solution for fitting the mixing model, with each iteration reducing the differences between the model and the data.

In an aspect, the fitting algorithm can be configured with a maximum number of iterations. For example, the mixture model can be fit using the maximum number of iterations (e.g., 30, 40, 50). In some scenarios the fitting algorithm can use less than the maximum number of iterations. For example, a heuristic can be used to detect early convergence. In the case of the EM algorithm, which is a local optimization procedure, it can be estimated that the initial values of $\mu_{DIP}$ and $\sigma_{DIP}$ may decrease the chance that the fitting algorithm converges to a non-global optimum. In some scenarios, $\mu_{DIP}$ can be initialized as the median coverage across all samples for the region in question (e.g., in regions where the median sample is haploid, the iterations may eventually reach the proper diploid mean). In an aspect, $\sigma_{DIP}$ can be initialized to the median absolute deviation (MAD) of the coverage values around the median of the coverage values, scaled by a constant factor to achieve asymptotic normality (e.g., compare the "mad" function in R).

Samples that have low likelihoods for all considered copy number states (e.g., less than $2.5\sigma$ from the mean) can be flagged as outliers for purposes of model-fitting. If a region has outlier samples, the mixture model can be retrained with the outlier coverage values removed.

At step 208, one or more copy number variants (CNVs) can be identified (e.g., determined, predicted, estimated) according to a Hidden Markov Model (HMM), a Bayesian network, and/or other probabilistic models based on the normalized sample coverage data and the fitted mixture model. For example, identifying one or more copy number variants according to a Hidden Markov Model (HMM)

based on the normalized sample coverage data and the fitted mixture model can comprise inputting the normalized sample coverage data for each calling window (e.g., of the one or more calling windows) into the HMM.

In another aspect, identifying one or more copy number variants according to a Hidden Markov Model (HMM) based on the normalized sample coverage data and the fitted mixture model can comprise determining one or more emission probabilities of the HMM based on the mixture model. For example, a probability of observing a normalized coverage value x, at a calling window w (e.g., of the one or more calling windows), given HMM state s, based on a component of the mixture model for w that corresponds to state s can be determined.

In another aspect, identifying one or more copy number variants according to a Hidden Markov Model (HMM) based on the normalized sample coverage data and the fitted mixture model can comprise identifying a calling window (e.g., of the one or more calling windows) as a CNV if a maximum likelihood sequence of states of the calling window is non-diploid. For example, a Viterbi algorithm can be performed in a 5' to 3' direction on a genomic region of the plurality of genomic regions. The Viterbi algorithm can be performed in a 3' to 5' direction the genomic region of the plurality of genomic region. A calling window (e.g., of the one or more calling windows) can be identified as a CNV if the genomic region of the plurality of genomic regions associated with the calling window has a most-likely state of non-diploid in the 5' to 3' direction and the 3' to 5' direction.

In an aspect the HMM can comprise a statistical Markov model in which the system being modeled is assumed to be a Markov process with unobserved (e.g., hidden) states. The hidden state space can comprise one of N possible values, modeled as a categorical distribution. The HMM can comprise transition probabilities. For each of N possible states that a hidden variable at time t can be in, there can be a transition probability from this state to each of the possible states of the hidden variable at time t+1, for a total of transition $N^2$ probabilities. The HMM can also comprise emission probabilities (e.g., for each of the N possible states) that govern the distribution of the observed variable at a particular time given the state of the hidden variable at that time.

The input to the HMM can be the normalized coverage values (e.g., from the within-sample procedure described previously) for an individual sample at each calling window. For example, the states of the HMM can comprise DEL (deletion), DIP (diploid), DUP (duplication), and/or the like. In some scenarios, the distinction between copy numbers 0 and 1 can be made in a post-processing step after DEL calls have been made.

In an aspect, the HMM can comprise transition probabilities as input values. The transition probabilities can be based on those used in XHMM. For example, the transition probabilities of XHMM, except the parameter 1/q (e.g., the mean of the prior geometric distribution of the number windows in a CNV), can be set to 0 (e.g., q=∞). For example, the transition probability can be similar (e.g., roughly the same as XHMM (non-zero)) to parameters of XHMM with the exception of the XHMM parameter 1/q, which can be set to 0 by setting q equal to infinity. The effect of this setting is that the HMM can be configured to place no prior assumptions on the number of windows in a CNV. Instead the HMM can be configured to only use the exponentially-distributed attenuation factor which is based on actual genomic distance. In an aspect, setting the XHMM parameter 1/q to zero can result in the following two assumptions: 1) DEL and DUP are equally likely, and 2) the size of CNVs is exponentially distributed. The teachings related to the XHMM as taught by Fromer et al. (2012), "Discovery and statistical genotyping of copy-number variation from whole-exome sequencing depth." Am J Hum Genet, 91 (4), 597-607, are specifically incorporated herein by reference.

In an aspect, the HMM can comprise emission probabilities as input values. The emission probabilities can be derived from the mixture models. For example, the probability of observing a (e.g., normalized) coverage value x, at a calling window w, given HMM state s, can be given by the component of the mixture model trained at w, that corresponds to state s. For the DEL state, a likelihood-weighted average of the probabilities given copy number 0 and 1 can be used. For example, if L(CN=1|cov)=9*L(CN=0|cov), then the emission probability can be 0.9*P(cov|CN=1)+ 0.1*P(cov|CN=0).

Using this Hidden Markov Model, the present methods and systems can be configured to identify CNVs. For example, the present methods and systems can be configured to identify CNV as regions where the maximum-likelihood sequence of states (e.g., predicted by the Viterbi algorithm or other appropriate algorithm) is non-diploid. It should be noted that running the Viterbi algorithm in only one direction may introduce a directional bias to the CNV calls. There is effectively a high cost to "open" a CNV but a low cost of "extending" the CNV. Thus, the called CNV regions may tend to overshoot the trailing breakpoint. To solve this problem, the present methods and systems can be configured to only report as CNVs regions for which the most-likely state is non-diploid in both a run of the Viterbi algorithm in the 5' to 3' direction and a run in 3' to 5' direction.

In an aspect, for each discovered CNV, five quality metrics can be computed based on probabilities from the Forward-Backward algorithm: $Q_{any}$, the phred-scaled probability that the region contains any CNV; $Q_{extend\ left}$ and $Q_{extend\ right}$, phred-scaled probabilities that the true CNV extends at least one window further upstream/downstream from the called region; and $Q_{contract\ left}$ and $Q_{contract\ right}$, phred-scaled probabilities that the true CNV is contracted compared to the called region by at least one window upstream or downstream.

It should be noted that even with the a priori filtering of windows with GC-content outside of the threshold range (e.g., [0.3, 0.7]) as described above, high rates of stochastic sequencing artifacts may still occur at the extreme ends of this threshold range. The Viterbi and Forward-Backward algorithms can be modified (e.g., configured) to place less credence on windows with "moderately-extreme" GC-content without ignoring these windows entirely. This configuration can be accomplished by multiplying the log-emission-probability for all states at a given window by a weight in the range [0, 1] based on the GC-content of the window. This configuration can reduce the relative significance of the data (e.g., observed coverage) at this window compared to the prior window (e.g., encoded by the state transition probabilities). As an illustration, for GC-fraction f in the default a priori valid range of [0.3, 0.7], the window weight can be set equal to $(1-(5*abs(f-0.5))^{18})^{18}$. The high polynomial term can be make the curve flat for non-extreme GC (e.g., weight=0.99993 for f=0.4), but drop sharply at the edges of the valid GC range (e.g., weight=0.5 for f=0.3333).

In an aspect, the present methods and systems can fit models and make CNV calls for regions on the sex chromosomes if the sex of each input sample is provided. Basing the expected copy number (e.g., diploid or haploid) on sex explicitly can be more effective than normalizing the variance due to sex or comparing samples to highly-correlated samples because such approach accounts for the integer nature of copy number states. As an illustration, a female with 0.5× the expected coverage for a region on chrX is likely to have a heterozygous deletion. A male with the same level of coverage may not be likely to have a heterozygous deletion, because one cannot have a copy number of 1/2.

Figure 15:
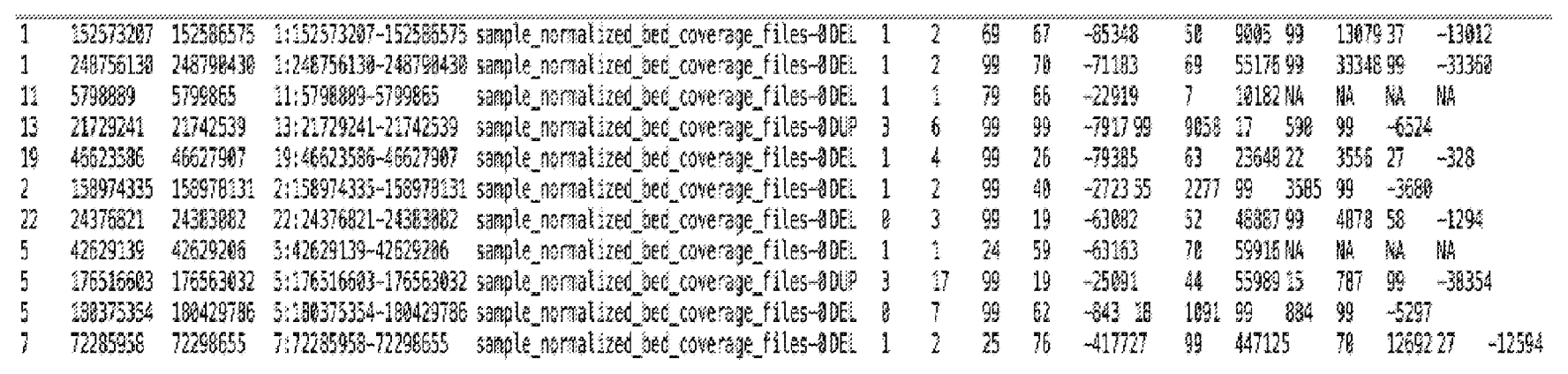

At step 210, the one or more copy number variants can be output. For example, the one or more copy number variants can be output to a user (e.g., via a user interface). The one or more copy number variants can be transmitted via a network to remote location. The one or more copy number variants can be provided as input to another executable program. The one or more copy number variants can be stored in a storage location, such as a database, or other file format. Example output is shown in FIG. 15.

Figure 5:
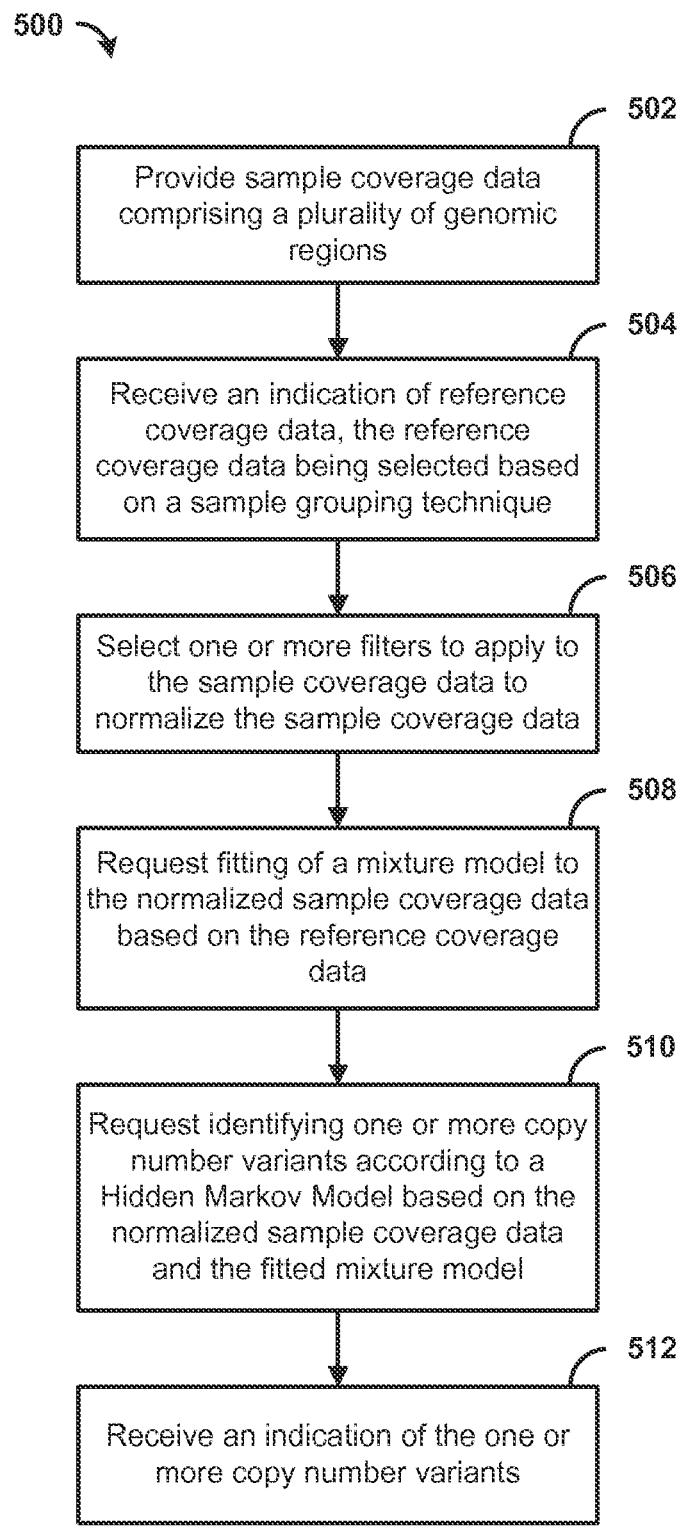
FIG. 5 is a flow chart illustrating another example method for estimating copy number variants.

FIG. 5 is a flow chart illustrating another example method 500 for estimating copy number variants. At step 502, sample coverage data comprising a plurality of genomic regions can be provided (e.g., by a user, from a first device to a second device). In an aspect, the plurality of genomic regions can be divided into one or more calling windows (e.g., a plurality of calling windows). For example, only genomic regions of the plurality of genomic regions larger than a predetermined size may be divided.

At step 504, an indication of reference coverage data can be received (e.g., by a user, from a first device to a second device). The reference coverage data can be selected based on a sample grouping technique. For example, the sample grouping technique can comprise a technique (e.g., algorithm) for grouping samples by similarity. The sample grouping technique can comprise a clustering algorithm, a classification algorithm, a combination thereof, and/or the like. For example, the sample grouping technique can comprise receiving a plurality of metrics for the sample coverage data, defining a distance metric between the sample coverage data and the reference coverage data based on the plurality of metrics, selecting the reference coverage data for each sample based on the distance metric, and/or the like.

As an illustration, the sample grouping technique can comprise a k-Nearest Neighbors (knn) algorithm. Selecting reference coverage data based on the sample grouping technique can comprise one or more of: scaling a plurality of metrics associated with the reference coverage data, generating a k-d tree based on the scaled plurality of metrics associated with the reference coverage data, scaling a plurality of metrics associated with the sample coverage data, adding the sample coverage data to the k-d tree based on the scaled plurality of metrics associated with the sample coverage data, identifying a predetermined number of nearest neighbors to the sample coverage data as the selected reference coverage data, and/or the like.

At step 506, one or more filters can be selected (e.g., by a user, by the first device and/or the second device) to apply to the sample coverage data to normalize the sample coverage data. For example, the sample coverage data can be filtered. The one or more filters can be configured for one or more of: filtering the one or more calling windows based on a level of GC content, filtering the one or more calling windows based on a mappability score of a genomic region of the plurality of genomic regions, filtering the one or more calling windows based on a measure of central tendency of read coverage, filtering the one or more calling windows based on occurrence of a calling window in a multi-copy duplication genomic region, and/or the like.

In an aspect, filtering the one or more calling windows based on a level of GC content can comprise excluding a calling window of the one or more calling windows if the level of GC content of the calling window is outside a predetermined range.

In an aspect, filtering the one or more calling windows based on a mappability score can comprise determining a mappability score for each genomic region of the plurality of genomic regions. For example, determining a mappability score for each genomic region of the plurality of genomic regions can comprise determining an average of an inverse reference-genome frequency of k-mers whose first base overlaps the genomic region of the plurality of genomic regions. Filtering the one or more calling windows based on a mappability score can further comprise excluding a calling window of the one or more calling windows that contains the genomic region of the plurality of genomic regions if the mappability score of the genomic region of the plurality of genomic regions is below a predetermined threshold.

In an aspect, filtering the one or more calling windows based on a measure of central tendency of read coverage can comprise excluding a calling window of the one or more calling windows if the calling window of the one or more calling windows comprises a measure of central tendency of read coverage less than an expected coverage value for calling windows with similar GC content.

In an aspect, filtering the one or more calling windows based on occurrence of a calling window in a multi-copy duplication genomic region can comprise excluding a calling window of the one or more calling windows if the calling window of the one or more calling windows occurs within a region where multi-copy duplications are known to be present.

In an aspect, filtering and/or normalizing can comprise one or more of determining raw coverage for a calling window w, determining a median coverage for the sample coverage data across the one or more calling windows conditional on a GC-fraction of the calling window w, dividing the raw coverage by the median coverage (e.g., resulting in the normalized sample coverage data), and/or the like. For example, determining a median coverage for the sample coverage data across the plurality of windows conditional on a GC-fraction of the calling window w can comprise one or more of: binning the one or more calling windows by GC-fraction (e.g., resulting in a plurality of bins), determining a median coverage for each bin of the plurality of bins, determining a normalizing factor for each distinct possible GC-fraction using a linear interpolation between the median coverage for two bins nearest to the calling window w, and/or the like.

At step 508, fitting of a mixture model to the normalized sample coverage data based on the reference coverage data can be requested (e.g., by a user, from the first device to the second device). For example, training of the mixture model according to the selected reference coverage data can be requested. Fitting the mixture model to the normalized sample coverage data based on the reference coverage data can comprise determining a plurality of mixture models, one for each of the plurality of genomic regions. Each component of the plurality of mixture models can comprise a probability distribution that represents an expected normalized coverage conditional on a particular copy number. Fitting the mixture model to the normalized sample coverage data based on the reference coverage data can comprise fitting the plurality of mixture models to the normalized sample coverage data using an expectation-maximization algorithm to determine a likelihood for each copy number at each of the one or more calling windows. The selected reference coverage data can be input to the expectation-maximization algorithm.

At step 510, one or more copy number variants can be identified (e.g., by the user, by the first device, by the second device) according to a Hidden Markov Model (HMM) based on the normalized sample coverage data and the fitted mixture model. For example, identifying one or more copy number variants according to a Hidden Markov Model (HMM) based on the normalized sample coverage data and the fitted mixture model can comprise one or more of inputting the normalized sample coverage data for each calling window (e.g., of the one or more calling windows) into the HMM, determining one or more emission probabilities of the HMM based on the mixture model, identifying a calling window (e.g., of the one or more calling windows) as a CNV if a maximum likelihood sequence of states of the calling window is non-diploid, and/or the like.

In an aspect, determining one or more emission probabilities of the HMM based on the mixture model can comprise determining a probability of observing a normalized coverage value x, at a calling window w (e.g., of the one or more calling windows), given HMM state s, based on a component of the mixture model for w that corresponds to state s.

In an aspect, identifying a calling window (e.g., of the one or more calling windows) as a CNV if a maximum likelihood sequence of states of the calling window is non-diploid can comprise one or more of performing a Viterbi algorithm in a 5' to 3' direction on a genomic region of the plurality of genomic regions, performing the Viterbi algorithm in a 3' to 5' direction the genomic region of the plurality of genomic regions, identifying a calling window (e.g., of the one or more calling windows) as a CNV if the genomic region of the plurality of genomic regions associated with the calling window has a most-likely state of non-diploid in the 5' to 3' direction and the 3' to 5' direction, and/or the like.

At step 512, an indication of the one or more copy number variants can be received (e.g., by a user, by the first device, by the second device). For example, the indication can be provided to a display, via a network, and/or the like. An example indication of the one or more copy number variants is shown in FIG. 15.

Figure 6:
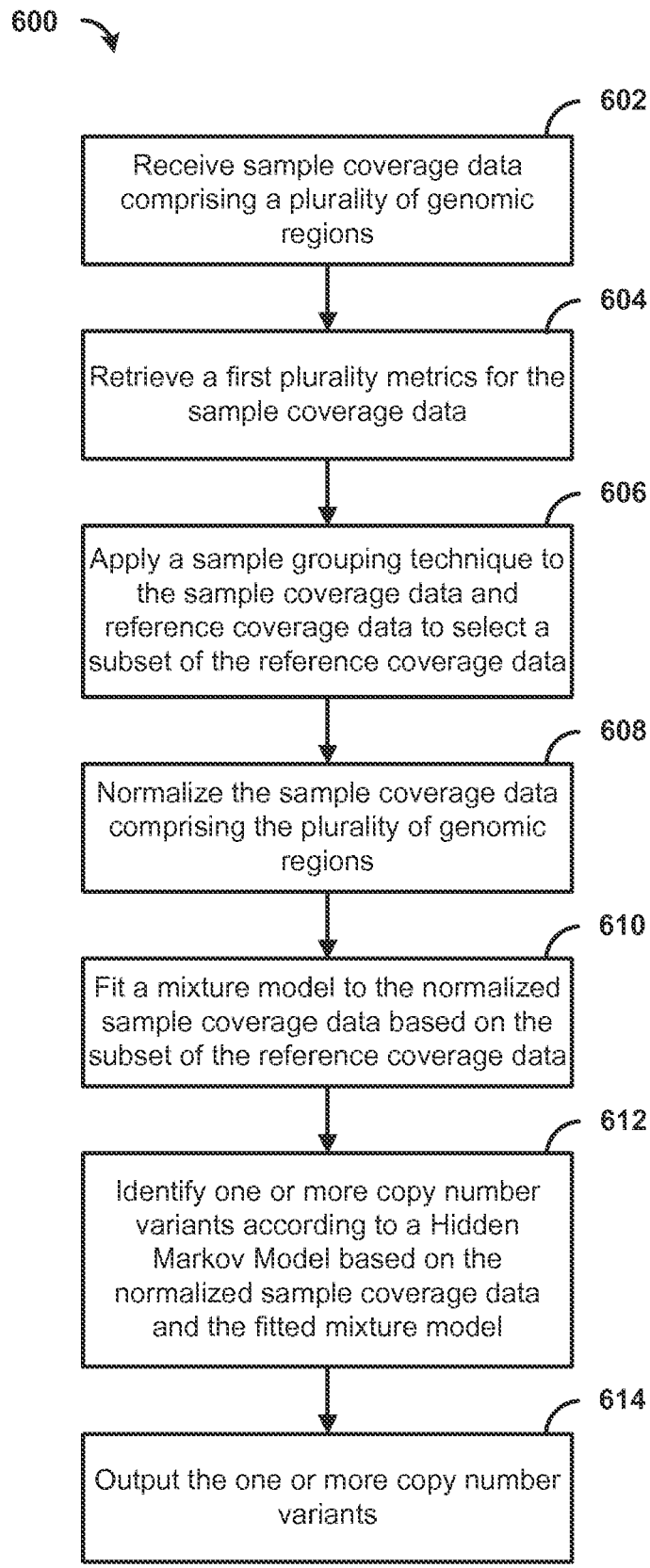
FIG. 6 is a flow chart illustrating yet another example method for estimating copy number variants.

FIG. 6 is a flow chart illustrating yet another example method 600 for estimating copy number variants. At step 602, sample coverage data comprising a plurality of genomic regions can be received. In an aspect, the plurality of genomic regions can be divided into one or more calling windows (e.g., a plurality of calling windows). For example, only genomic regions of the plurality of genomic regions larger than a predetermined size may be divided.

In an aspect, the sample coverage data can be filtered. For example, filtering the sample coverage data can comprise one or more of filtering the one or more calling windows based on a level of GC content, filtering the one or more calling windows based on a mappability score of a genomic region of the plurality of genomic regions, filtering the one or more calling windows based on a measure of central tendency of read coverage, filtering the one or more calling windows based on occurrence of a calling window in a multi-copy duplication genomic region, and/or the like.

In an aspect, filtering the one or more calling windows based on a level of GC content can comprise excluding a calling window of the one or more calling windows if the level of GC content of the calling window is outside a predetermined range. Filtering the one or more calling windows based on a mappability score can comprise determining a mappability score for each genomic region of the plurality of genomic regions. For example, determining a mappability score for each genomic region of the plurality of genomic regions can comprise determining an average of an inverse reference-genome frequency of k-mers whose first base overlaps the genomic region of the plurality of genomic regions. Filtering the one or more calling windows based on a mappability score can further comprise excluding a calling window of the one or more calling windows that contains the genomic region of the plurality of genomic regions if the mappability score of the genomic region of the plurality of genomic regions is below a predetermined threshold.

In an aspect, filtering the one or more calling windows based on a measure of central tendency of read coverage can comprise excluding a calling window of the one or more calling windows if the calling window of the one or more calling windows comprises a measure of central tendency of read coverage less than an expected coverage value for calling windows with similar GC content. Filtering the one or more calling windows based on occurrence of a calling window in a multi-copy duplication genomic region can comprise excluding a calling window of the one or more calling windows if the calling window of the one or more calling windows occurs within a region where multi-copy duplications are known to be present.

At step 604, a first plurality of metrics for the sample coverage data can be retrieved. The first plurality of metrics can comprise, for example, sequencing quality control (QC) metrics, sample metadata, ancestry-based values, sequence-similarity scores, and/or any metric that captures sample-level variability. For example, in the case of sequencing QC metrics, seven QC metrics can be used. As an illustration, the sequencing QC metrics can comprise GCDROPOUT, ATDROPOUT, MEANINSERTSIZE, ONBAITVSSELECTED, PCTPFUQREADS, PCTTARGETBASES10X, PCTTARGETBASES50X, and/or the like. The sequencing QC metrics can be scaled (e.g., by applying a linear transform) and processed to build a k-d tree.

At step 606, a sample grouping technique can be applied to the sample coverage data and reference coverage data to select a subset of the reference coverage data. The sample grouping technique can comprise a technique (e.g., algorithm) for grouping samples by similarity. For example, the sample grouping technique can comprise a clustering algorithm, a classification algorithm, a combination thereof, and/or the like. In an aspect, applying a sample grouping technique to the sample coverage data and reference coverage data to select a subset of the reference coverage data can comprise defining a distance metric between the sample coverage data and the reference coverage data based on the first plurality of metrics. The reference coverage data can be selected for each sample based on the distance metric.

As another example, the sample grouping technique can comprise a k-Nearest Neighbors (knn) algorithm. Applying the sample grouping technique to the sample coverage data and reference coverage data to select a subset of the reference coverage data can comprise one or more of: retrieving a second plurality of metrics associated with the reference coverage data, scaling the second plurality of metrics associated with the reference coverage data, generating a k-d tree based on the scaled second plurality of metrics associated with the reference coverage data, scaling the first plurality of metrics for the sample coverage data, adding the sample coverage data to the k-d tree based on the scaled first plurality of metrics for the sample coverage data, identifying a predetermined number of nearest neighbors to the sample coverage data as the subset of the reference coverage data, and/or the like.

At step 608, the sample coverage data comprising the plurality of genomic regions can be normalized. For example, normalizing the sample coverage data comprising the plurality of genomic regions can comprise one or more of determining raw coverage for a calling window w, determining a median coverage for the sample coverage data across the one or more calling windows conditional on a GC-fraction of the calling window w; dividing the raw coverage by the median coverage (e.g., resulting in the normalized sample coverage data), and/or the like.

In an aspect, determining a median coverage for the sample coverage data across the plurality of windows conditional on a GC-fraction of the calling window w can comprise one or more of binning the one or more calling windows by GC-fraction (e.g., resulting in a plurality of bins), determining a median coverage for each bin of the plurality of bins, determining a normalizing factor for each distinct possible GC-fraction using a linear interpolation between the median coverage for two bins nearest to the calling window w, and/or the like.

At step 610, a mixture model can be fit to the normalized sample coverage data based on the subset of the reference coverage data. For example, the mixture model can be trained according to the subset of the reference coverage data. Fitting the mixture model to the normalized sample coverage data based on the subset of the reference coverage data can comprise determining a plurality of mixture models, one for each of the plurality of genomic regions. One or more (or each) component of the plurality of mixture models can comprise a probability distribution that represents an expected normalized coverage conditional on a particular copy number. Fitting the mixture model to the normalized sample coverage data based on the subset of the reference coverage data can also comprise fitting the plurality of mixture models to the normalized sample coverage data using an expectation-maximization algorithm to determine a likelihood for each copy number at each of the one or more calling windows. The subset of the reference coverage data can be input to the expectation-maximization algorithm.

At step 612, one or more copy number variants can be identified according to a Hidden Markov Model (HMM) based on the normalized sample coverage data and the fitted mixture model. For example, identifying one or more copy number variants according to a Hidden Markov Model (HMM) based on the normalized sample coverage data and the fitted mixture model can comprise one or more of inputting the normalized sample coverage data for each calling window (e.g., of the one or more calling windows) into the HMM, determining one or more emission probabilities of the HMM based on the mixture model, identifying a calling window (e.g., of the one or more calling windows) as a CNV if a maximum likelihood sequence of states of the calling window is non-diploid, and/or the like. In an aspect, determining one or more emission probabilities of the HMM based on the mixture model can comprise determining a probability of observing a normalized coverage value x, at a calling window w (e.g., of the one or more calling windows), given HMM state s, based on a component of the mixture model for w that corresponds to state s.

In an aspect, identifying a calling window (e.g., of the one or more calling windows) as a CNV if a maximum likelihood sequence of states of the calling window is non-diploid can comprise one or more of: performing a Viterbi algorithm in a 5' to 3' direction on a genomic region of the plurality of genomic regions, performing the Viterbi algorithm in a 3' to 5' direction the genomic region of the plurality of genomic regions, identifying a calling window (e.g., of the one or more calling windows) as a CNV if the genomic region of the plurality of genomic regions associated with the calling window has a most-likely state of non-diploid in the 5' to 3' direction and the 3' to 5' direction, and/or the like.

At step 614, the one or more copy number variants can be output. For example, the one or more copy number variants can be output to a user (e.g., via a user interface). The one or more copy number variants can be transmitted via a network to remote location. The one or more copy number variants can be provided as input to another executable program. The one or more copy number variants can be stored in a storage location, such as a database, or other file format. Example output is shown in FIG. 15.

Figure 7:
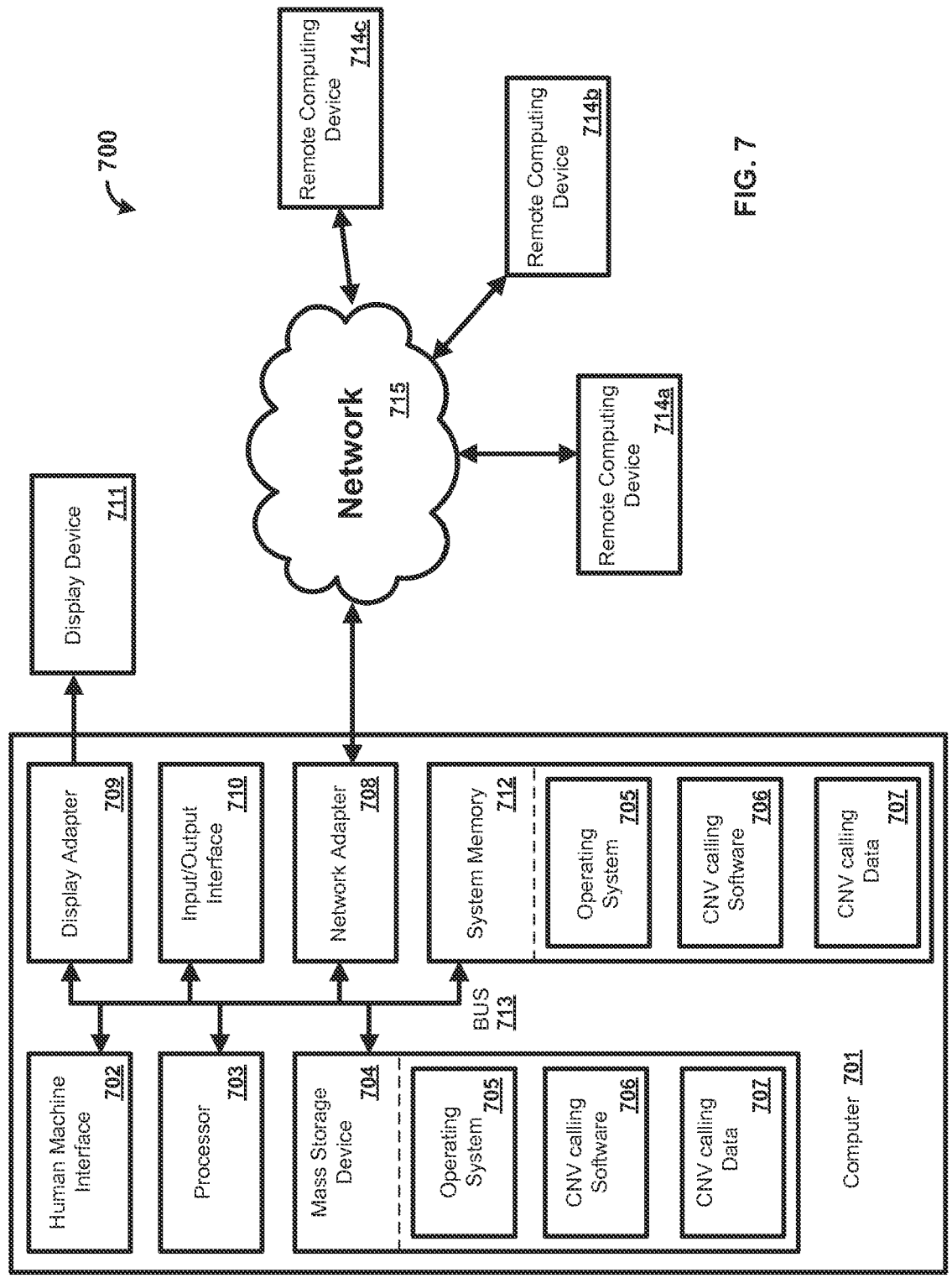
FIG. 7 is a block diagram illustrating an exemplary operating environment for performing the disclosed methods.

In an exemplary aspect, the methods and systems can be implemented on a computer 701 as illustrated in FIG. 7 and described below. Similarly, the methods and systems disclosed can utilize one or more computers to perform one or more functions in one or more locations. FIG. 7 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 701. The components of the computer 701 can comprise, but are not limited to, one or more processors 703, a system memory 712, and a system bus 713 that couples various system components including the one or more processors 703 to the system memory 712. The system can utilize parallel computing.

The system bus 713 represents one or more of several possible types of bus structures, including a memory bus or memory controller, a peripheral bus, an accelerated graphics port, or local bus using any of a variety of bus architectures.

By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCM-CIA), Universal Serial Bus (USB) and the like. The bus 713, and all buses specified in this description can also be implemented over a wired or wireless network connection and each of the subsystems, including the one or more processors 703, a mass storage device 704, an operating system 705, CNV calling software 706, CNV calling data 707, a network adapter 708, the system memory 712, an Input/Output Interface 710, a display adapter 709, a display device 711, and a human machine interface 702, can be contained within one or more remote computing devices 714a,b,c at physically separate locations, connected through buses of this form, in effect implementing a fully distributed system.

The computer 701 typically comprises a variety of computer readable media. Exemplary readable media can be any available media that is accessible by the computer 701 and comprises, for example and not meant to be limiting, both volatile and non-volatile media, removable and non-removable media. The system memory 712 comprises computer readable media in the form of volatile memory, such as random access memory (RAM), and/or non-volatile memory, such as read only memory (ROM). The system memory 712 typically contains data such as the CNV calling data 707 and/or program modules such as the operating system 705 and the CNV calling software 706 that are immediately accessible to and/or are presently operated on by the one or more processors 703.

In another aspect, the computer 701 can also comprise other removable/non-removable, volatile/non-volatile computer storage media. By way of example, FIG. 7 illustrates the mass storage device 704 which can provide non-volatile storage of computer code, computer readable instructions, data structures, program modules, and other data for the computer 701. For example and not meant to be limiting, the mass storage device 704 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 704, including by way of example, the operating system 705 and the CNV calling software 706. Each of the operating system 705 and the CNV calling software 706 (or some combination thereof) can comprise elements of the programming and the CNV calling software 706. The CNV calling data 707 can also be stored on the mass storage device 704. The CNV calling data 707 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 701 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the one or more processors 703 via the human machine interface 702 that is coupled to the system bus 713, but can be connected by other interface and bus structures, such as a parallel port, game port, an IEEE 1394 Port (also known as a Firewire port), a serial port, or a universal serial bus (USB).

In yet another aspect, the display device 711 can also be connected to the system bus 713 via an interface, such as the display adapter 709. It is contemplated that the computer 701 can have more than one display adapter 709 and the computer 701 can have more than one display device 711. For example, a display device can be a monitor, an LCD (Liquid Crystal Display), or a projector. In addition to the display device 711, other output peripheral devices can comprise components such as speakers (not shown) and a printer (not shown) which can be connected to the computer 701 via the Input/Output Interface 710. Any step and/or result of the methods can be output in any form to an output device. Such output can be any form of visual representation, including, but not limited to, textual, graphical, animation, audio, tactile, and the like. The display 711 and computer 701 can be part of one device, or separate devices.

The computer 701 can operate in a networked environment using logical connections to one or more remote computing devices 714a,b,c. By way of example, a remote computing device can be a personal computer, portable computer, smartphone, a server, a router, a network computer, a peer device or other common network node, and so on. Logical connections between the computer 701 and a remote computing device 714a,b,c can be made via a network 715, such as a local area network (LAN) and/or a general wide area network (WAN). Such network connections can be through the network adapter 708. The network adapter 708 can be implemented in both wired and wireless environments. Such networking environments are conventional and commonplace in dwellings, offices, enterprise-wide computer networks, intranets, and the Internet.

For purposes of illustration, application programs and other executable program components such as the operating system 705 are illustrated herein as discrete blocks, although it is recognized that such programs and components reside at various times in different storage components of the computing device 701, and are executed by the one or more processors 703 of the computer. An implementation of the CNV calling software 706 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, etc.), but some errors and deviations should be accounted for.

The present methods and systems were validated using a variety of validation experiments. A first experiment evaluated the adherence of CNV calls from CLAMMS and other algorithms to Mendelian inheritance patterns on a pedigree. Calls from CLAMMS, XHMM (another widely-used algorithm), and SNP genotyping arrays for a set of 3164 samples are compared. Another validation experiment used TaqMan qPCR to validate CNVs predicted by CLAMMS. For example, TaqMan qPCR can be used as an illustration to validate CLAMMS at 37 loci (95% of rare variants validate), across 17 common variant loci. The mean precision and recall are 99% and 94%, respectively.

Validation of the present method and systems included analysis of the complexity of operation and scalability of the CLAMMS algorithm. For example, sequencing n samples may take O(n log n) time, as maintaining the k-d tree takes only O(log n) time per sample. This approach improves on the $O(n^2)$ complexity of previous algorithms (e.g., both PCA and the reference-panel selection methods of CANOES and ExomeDepth require the coverage profile of each sample to be compared to every other sample).

As described further herein the adherence of CNV calls from CLAMMS, XHMM, CoNIFER, CANOES, and ExomeDepth to Mendelian inheritance patterns can be evaluated. As an illustration, the adherence of CNV calls from these algorithms were evaluated for eight members of the CEPH pedigree 1463, sequenced in three technical replicates. 92 additional samples were provided as a reference panel. It should be noted that most CNVs in the pedigree are common variants (e.g., by definition). 98% of calls were inherited and 94% were consistent across all three technical replicates. Statistics for other evaluated algorithms are presented further below.

The CLAMMS algorithm's improved performance for common CNVs does not come at a cost of reduced performance for rare CNVs. For example, as another validation experiment CNV calls from CLAMMS and XHMM were compared against "gold-standard" calls from PennCNV (e.g., which uses data from SNP genotyping arrays) for 3164 samples. The PennCNV calls were subject to several quality-control filters. For rare variants (e.g., AF≤0.1% in the array data), CLAMMS had 78% precision and 65% recall, compared to XHMM's 66% precision and 64% recall.

As another validation experiment, TaqMan qPCR can be used to validate a random subset of CNVs predicted by CLAMMS. TaqMan qPCR was used to validate at 20 rare variant loci and 20 common variant loci that overlap disease-associated genes in the Human Gene Mutation Database. In this example validation experiment, 19/20 (95%) of the rare variants predicted by CLAMMS were validated. Three common variant loci were excluded due to high variance in the TaqMan data. The remaining 17 loci yielded mean precision/recall values of 99.0% and 94.1% respectively. As another result, 16/17 (94%) loci had no false positives. As a further result, 13/17 loci (76%) had greater than or equal to 90% sensitivity for 165 samples genotyped. FIG. 8 through FIG. 14 illustrate these validation experiments in greater detail.

Figure 8:
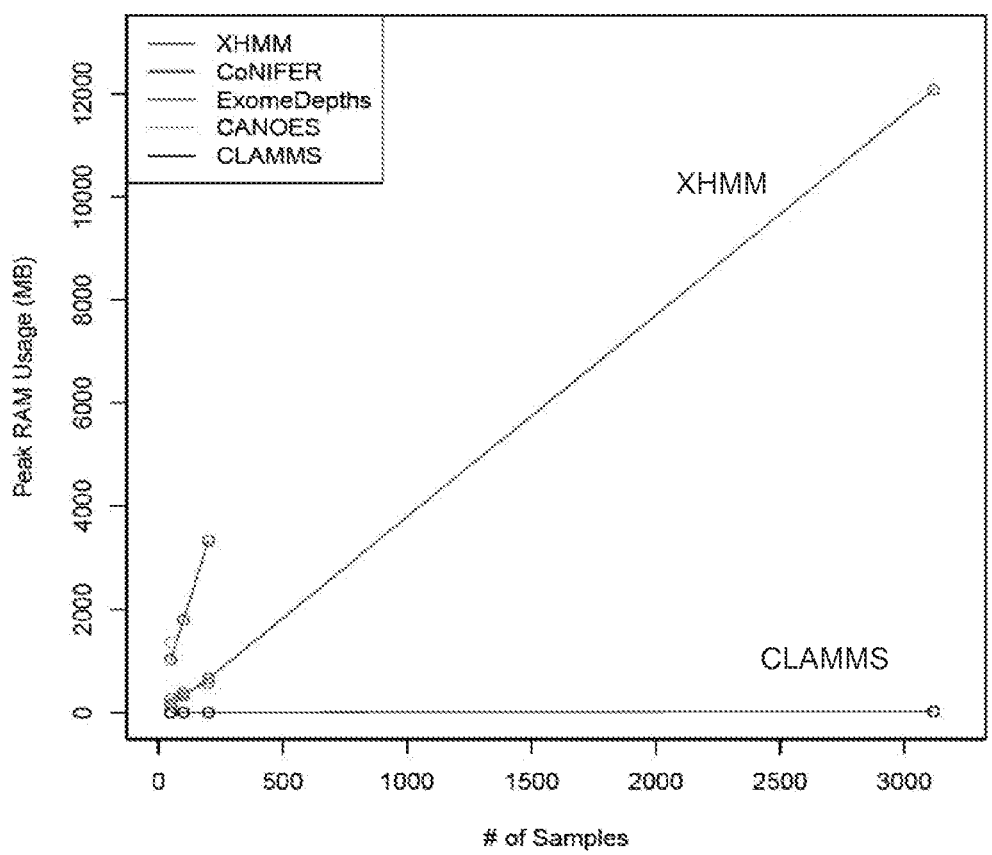
FIG. 8 compares the RAM usage of CLAMMS vs. other algorithms.

FIG. 8 compares the RAM usage of CLAMMS vs. other algorithms. The RAM usage of CLAMMs appears constant while the RAM usage of other algorithms increasing linearly with the number of samples. RAM usage of CNV-calling algorithms is shown for 50 samples for all algorithms. RAM usage of CNV-calling algorithms is shown for 100 and 200 samples with all algorithms but CANOES, which ran 4 hours without finishing. RAM usage is shown for 3164 samples using CLAMMS and XHMM.

In an aspect, the CLAMMs algorithm can be validated as follows. Validation can be performed, for example, using data from a repository, such as CEPH pedigree 1463. A first validation experiment was to evaluate the adherence of CNV calls from CLAMMS and four other algorithms (XHMM, CoNIFER, CANOES, and ExomeDepth) to Mendelian inheritance patterns on an 8-member pedigree (e.g., a subset of CEPH pedigree 1463, including grandparents NA12889, NA12890, NA12891, NA12892; parents NA12877, NA12878; and children NA12880, NA12882). Each of the 8 pedigree members were sequenced in three technical replicates. CNV calls were made using each algorithm's default parameters as described herein. A reference panel of 92 unrelated samples were made available to each algorithm. To ensure a fair comparison, the a-priori filters used by CLAMMS (e.g., filtering extreme-GC and low-mappability regions) can be applied to the input data for all algorithms, so differences in performance may not be attributed to CLAMMS' exclusion of the most problematic genomic regions. Sex chromosomes were also excluded from the comparison.

Three evaluation metrics can be computed for each algorithm: 1) the proportion of calls that were consistent across all 3 technical replicates, 2) the transmission rate of calls in the 1st and 2nd generations, and 3) the proportion of calls in the 2nd and 3rd generations that were inherited. A 50% overlap criterion was used when determining whether a call is transmitted and/or inherited (e.g., a CNV in a child is inherited if any CNV in its parents overlaps at least 50% of it).

FIG. 9 is a table illustrating performance metrics for CNV calls on the CEPH pedigree. The #Calls column is for the 8 pedigree members across 3 technical replicates (e.g., 24 samples in total). CNVs were classified as common if the CNV's allele frequency was greater than or equal to 1%, and classified as rare otherwise (e.g., note that rare CNVs may be false-positives). ExomeDepth calls can be excluded with Bayes Factor of less than 10 (e.g., or other threshold). FIG. 9 also shows the number of calls made by each algorithm, consistency across technical replicates, and corresponding Mendelian inheritance patterns. As previously explained, all of the algorithms mentioned except CLAMMS are focused exclusively on rare variants, assuming that reference panel samples are diploid (e.g., presenting a unimodal coverage distribution) at all loci. The poor performance of the other algorithms is therefore to be expected as most CNVs in the pedigree are common variants. CLAMMS on the other hand genotypes these common variants accurately (e.g., with only 2% of its calls being putatively de novo). The higher-than- Mendelian transmission rate (e.g., 61%) can simply be due to chance (e.g., there are only 27 unique CNV loci in the 1st and 2nd generations).

In an aspect, validation can be performed using "gold-standard" array-based CNV calls. Our second validation experiment was to compare CNV calls from CLAMMS and XHMM against "gold-standard" calls from PennCNV, that uses data from SNP genotyping arrays for a set of 3164 samples in the Regeneron Genetics Center's human exome variant database. Test set samples were excluded if any of the following test conditions were met: #PennCNV calls greater than 50, LRR_SD (standard deviation of log R ratio) greater than 0.23 (95th percentile), and BAF_drift (B-allele frequency drift) greater than 0.005 (95th percentile).

In an aspect, array-based CNV calls, despite generally being more accurate than CNV calls from exome sequencing read depth, may not be a true "gold-standard" and can include false positives, including several putative copy number polymorphic loci (e.g., AF greater than 1%) that did not overlap any variants in two published datasets (CNV calls from 849 whole genomes, and array-based CNV calls from 19,584 controls in an autism study). To minimize the false positive rate in the test set, only CNVs were included that were rare and not small. PennCNV calls were excluded for which one or more of the following conditions are met: CNV length less than 10 kb or greater than 2 Mb, CNV does not overlap at least 1 exon and at least 10 SNPs in the array design, the CNV overlaps a gap in the reference genome (e.g., GRCh37) or a common genomic rearrangement in HapMap, allele frequency greater than 0.1% specific data sets and/or or the 3,164 test samples (e.g., CNVs are included in the allele frequency count if they overlap at least 33.3% of the CNV in question).

The final test set after all filters have been applied can comprise 1,715 CNVs (e.g., 46% DEL, 54% DUP) in 1,240 samples. For this evaluation, both CLAMMS and XHMM were run with default parameters and procedures. It is recommended to consider samples with 2× the median number of calls for any particular dataset to be outliers. For this example dataset, the median number of CLAMMS calls/sample is 11. CLAMMS calls from 26 samples (e.g., 0.8% of the total) were excluded where CLAMMS performs greater than 22 calls. Array calls from these samples can still be included in the test set.

FIG. 10 shows CLAMMS & XHMM CNV calls compared to PennCNV "gold-standard." Precision can be calculated as the percentage of CLAMMS/XHMM calls that could possibly be supported by a PennCNV call—meaning that the two algorithms are subject to the same filtering criteria—that are in fact overlapped by a PennCNV call at the specified overlap threshold. The recall (e.g., sensitivity) can be calculated as the percentage of PennCNV calls that are overlapped by any CLAMMS/XHMM call (e.g., no filters applied) at the specified overlap threshold. F-score can be defined as the geometric mean of precision and recall.

In an aspect, CLAMMS can achieve an 9.3% higher F-score than XHMM using the any-overlap criterion, 5.8% higher using the 33%-overlap criterion, and 4.9% higher using the 50%-overlap criterion. This improvement is driven by CLAMMS' greater precision (e.g., 18%-20% greater depending on the overlap threshold).

CLAMMS is generally more conservative when estimating a CNV's breakpoints (e.g., reporting smaller CNVs) than PennCNV or XHMM, which is why recall is significantly greater using any overlap vs. 50% overlap. As discussed herein, algorithms including PennCNV and XHMM use the Viterbi algorithm to identify CNV regions, scanning across the exome in one direction (e.g., 5' to 3'). Such approach introduces directional bias into the CNV calls: there is effectively a high cost of "opening" a CNV but a low cost of "extending" the CNV, so the called CNV regions will tend to overshoot the 3'-end breakpoint. CLAMMS on the other hand can be configured to only report the intersection of the CNV regions called when Viterbi is run forwards (5' to 3') and backwards (3' to 5'), eliminating the directional bias.

In an aspect, validation can be performed using TaqMan qPCR as follows. TaqMan quantitative-PCR can be used to validate a selection of CNV loci (e.g., 20 rare, 20 common) predicted by CLAMMS. For each locus, the PCR-based copy number predictions can be compared to CLAMMS CNV genotypes for 56/165 samples for rare and common loci respectively. The CNV loci can be selected randomly from the set of all loci that overlapped at least one gene with a disease association recorded in the Human Gene Mutation Database.

Using this approach, 19/20 (95%) of the rare variants were validated. 3/20 common variant loci were plausibly correct, but had high variance in the PCR data, making the results ambiguous. 16/17 (94%) of the remaining common variant loci had no false positives and one locus had 5/6 calls correct. 13/17 (76%) non-ambiguous common variant loci had greater than or equal to 90% sensitivity (e.g., including 9/17 loci with 100% sensitivity). The other 4/17 had sensitivities of 87.5%, 87.3%, 81.5%, and 70.1%. The means of the precision/sensitivity values for the 17 loci were 99.0% and 94.1% respectively.

FIG. 11 shows a table illustrating Rare CNV TaqMan Validations. In this example validation, the 165 samples tested for common CNV loci were not randomly selected in an attempt to minimize the number of samples required to ensure that each locus had a reasonable number of samples with non-diploid copy number (e.g., which is why several loci in the table have exactly 10 predicted CNV).

Figure 13:
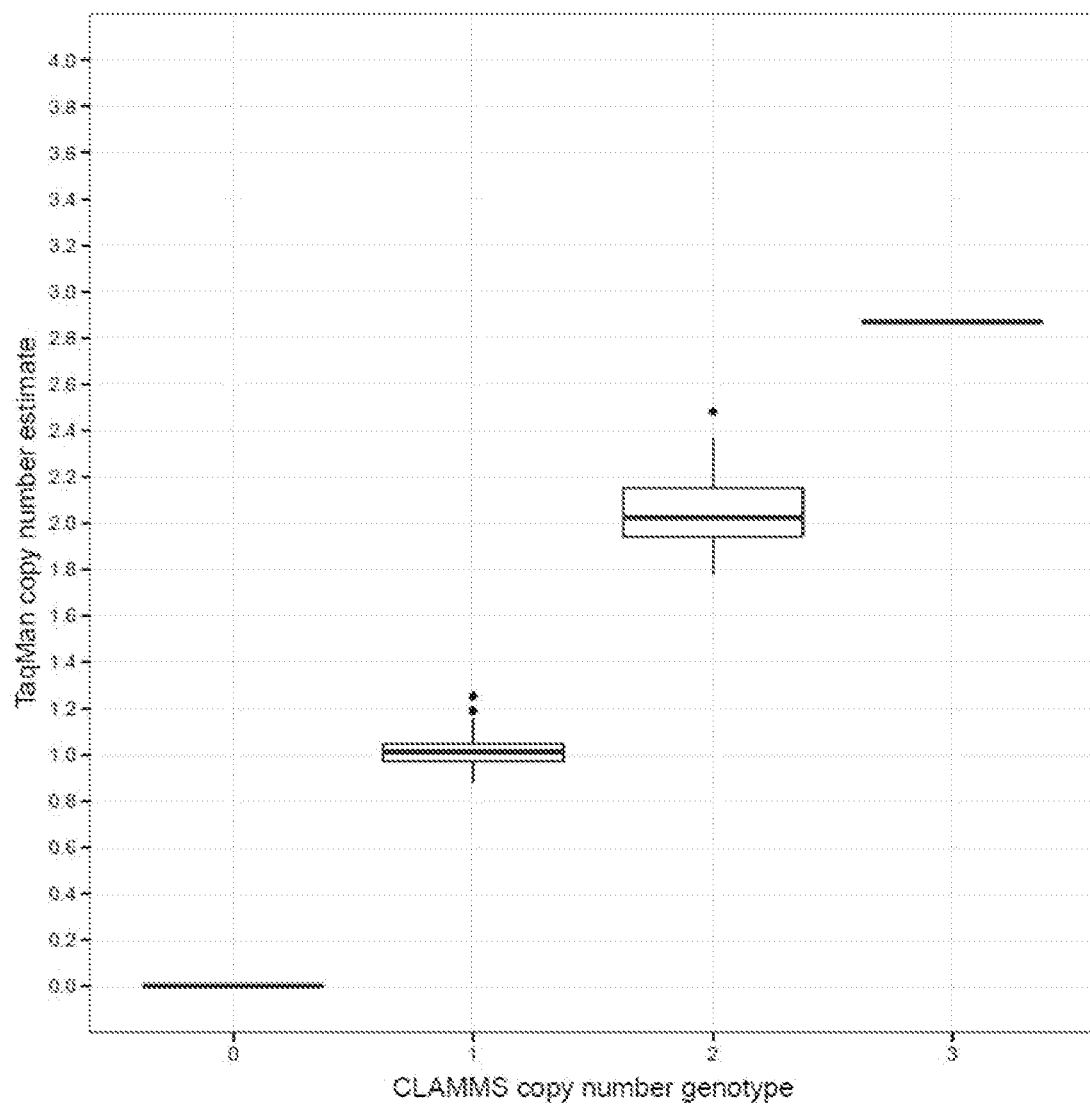
FIG. 13 is a graph comparing CLAMMS and TaqMan copy number predictions for the LILRA3 common variant locus.
Figure 14:
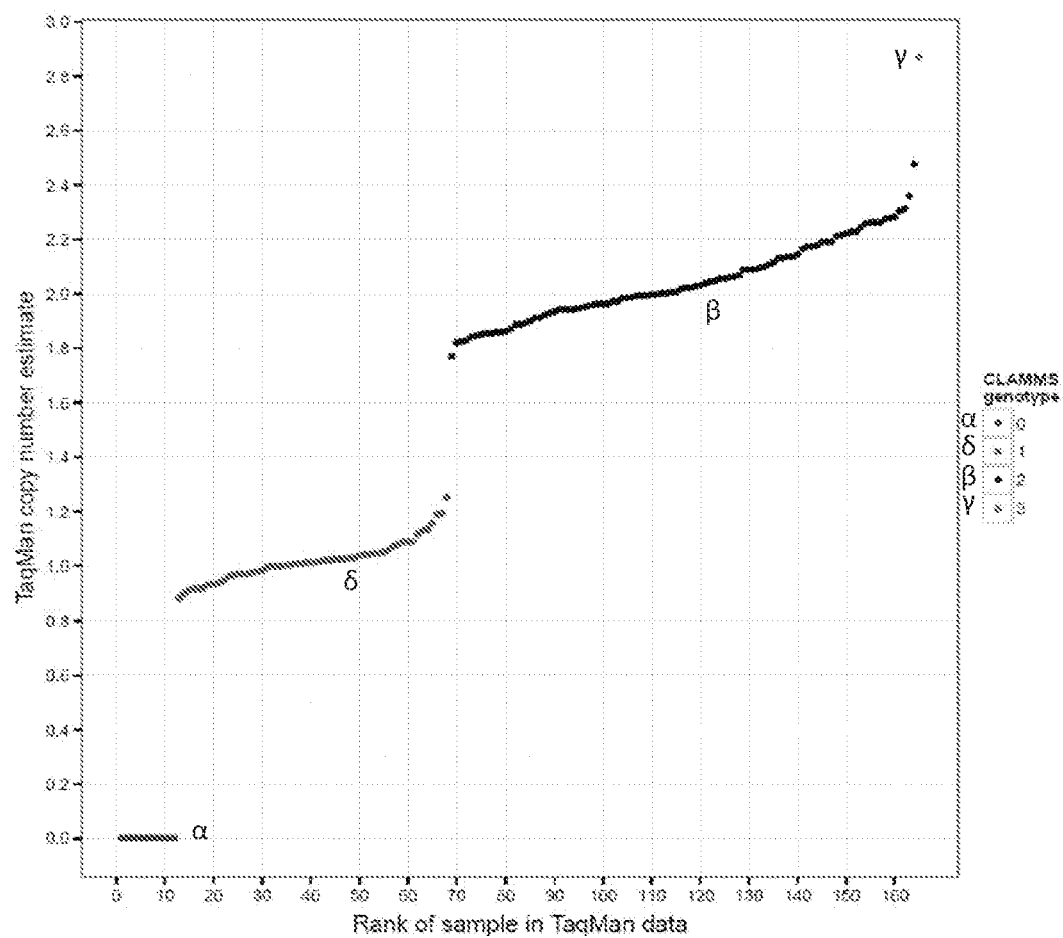
FIG. 14 is a graph comparing CLAMMS and TaqMan copy number predictions for the LILRA3 common variant locus.

FIG. 12 shows a table illustrating common CNV TaqMan Validations. FIG. 13 is a graph illustrating comparison of CLAMMS and TaqMan copy number predictions for the LILRA3 common variant locus. FIG. 14 is a graph illustrating comparison of CLAMMS and TaqMan copy number predictions for the LILRA3 common variant locus.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
receiving, by a computing device, a sample coverage data set comprising a plurality of genomic sequences obtained from sequencing of nucleic acid samples of a subject, and sample sequencing quality control (SSQC) metrics;
grouping, by the computing device, sets of sequencing quality control (SQC) metrics by a k-nearest neighbor algorithm into a k-d tree data structure according to similarity, wherein each of the sets of SQC metrics is associated with a respective reference coverage data set;
selecting, by the computing device, a reference panel of reference coverage data sets using the k-d tree data structure, wherein the selected reference coverage data sets have SQC metrics similar to the SSQC metrics; and
identifying one or more copy number variants (CNVs) by comparing, by the computing device, according to a Hidden Markov Model (HMM) and an expected coverage distribution from a mixture model, the sample coverage data set to the expected coverage distribution.

2. The method of claim 1, wherein selecting the reference panel of reference coverage data sets using the k-d tree data structure comprises:
defining a distance metric between the SSQC metrics and the SQC metrics; and
selecting the reference panel of the reference coverage data sets based on the distance metric.

3. The method of claim 1, wherein grouping the sets of SQC metrics comprises:
scaling the sets of SQC metrics of the reference coverage data sets;
scaling the SSQC metrics;
wherein grouping the sets of SQC metrics into the k-d tree data structure according to similarity comprises generating the k-d tree data structure based on the scaled sets of SQC metrics;
adding the scaled SSQC metrics to the k-d tree data structure; and
wherein selecting the reference panel of reference coverage data sets using the k-d tree data structure comprises identifying a predetermined number of nearest neighbors to the SSQC metrics as the selected reference coverage data sets.

4. The method of claim 1, wherein each respective reference coverage data set comprises a plurality of genomic regions, wherein the method further comprises dividing the plurality of genomic regions into one or more calling windows.

5. The method of claim 4, further comprising normalizing the sample coverage data set, wherein normalizing the sample coverage data set comprises:
determining raw coverage for a calling window w;
determining a median coverage for the sample coverage data set across the one or more calling windows conditional on a GC-fraction of the calling window w; and
dividing the raw coverage by the median coverage, resulting in a normalized sample coverage data set.

6. The method of claim 5, wherein determining the median coverage for the sample coverage data set across the one or more calling windows conditional on the GC-fraction of the calling window w comprises:
binning the one or more calling windows by GC-fraction, resulting in a plurality of bins;
determining a median coverage for each bin of the plurality of bins; and
determining a normalizing factor for each distinct possible GC-fraction using a linear interpolation between the median coverage for two bins nearest to the calling window w.

7. The method of claim 1, further comprising filtering the sample coverage data set.

8. The method of claim 7, wherein filtering the sample coverage data set comprises:
filtering one or more calling windows based on a mappability score of a genomic region of a plurality of genomic regions; and
filtering the one or more calling windows based on occurrence of a calling window in a multi-copy duplication genomic region.

9. The method of claim 8, wherein filtering the one or more calling windows based on the mappability score comprises:
determining a mappability score for each genomic region of the plurality of genomic regions; and
excluding a calling window of the one or more calling windows that contains the genomic region of the plurality of genomic regions if the mappability score of the genomic region of the plurality of genomic regions is below a predetermined threshold.

10. The method of claim 8, wherein filtering the one or more calling windows based on occurrence of the calling window in a multi-copy duplication genomic region comprises:
excluding a calling window of the one or more calling windows if the calling window of the one or more calling windows occurs within a region where multi-copy duplications are known to be present.

11. The method of claim 1, further comprising determining the expected coverage distribution from the mixture model wherein determining the expected coverage distribution from the mixture model comprises fitting the reference panel to the mixture model to determine the expected coverage distribution at each of a plurality of genomic regions wherein fitting the reference panel to the mixture model to determine the expected coverage distribution at each of the plurality of genomic regions comprises:
determining a plurality of mixture models, one for each of the plurality of genomic regions, wherein each component of the plurality of mixture models comprises a probability distribution that represents an expected coverage conditional on a particular copy number; and
fitting the plurality of mixture models to the reference panel using an expectation-maximization algorithm to determine a likelihood for each copy number at each of the one or more calling windows, wherein the reference panel is input to the expectation-maximization algorithm.

12. The method of claim 11, wherein identifying one or more copy number variants (CNVs) by comparing, according to the HMM and the expected coverage distribution from th mixture model, the sample coverage data set to the expected coverage distribution comprises:

inputting the sample coverage data set for each calling window of the one or more calling windows into the HMM;

determining one or more emission probabilities of the HMM based on the mixture model; and identifying a calling window of the one or more calling windows as a CNV if a maximum likelihood sequence of states of the calling window is non-diploid.

13. The method of claim 12, wherein determining one or more emission probabilities of the HMM based on the mixture model comprises:

determining a probability of observing a normalized coverage value x, at a calling window w of the one or more calling windows, given an HMM state s, based on a component of the mixture model for the calling window w that corresponds to the HMM state s.

14. The method of claim 12, wherein identifying the calling window of the one or more calling windows as a CNV if a maximum likelihood sequence of states of the calling window is non-diploid comprises:

performing a Viterbi algorithm in a 5' to 3' direction on a genomic region of the plurality of genomic regions;

performing the Viterbi algorithm in a 3' to 5' direction the genomic region of the plurality of genomic regions; and identifying the calling window of the one or more calling windows as a CNV if the genomic region of the plurality of genomic regions associated with the calling window has a most-likely state of non-diploid in the 5' to 3' direction and the 3' to 5' direction.

15. The method of claim 1, wherein selecting the reference panel of reference coverage data sets using the k-d tree data structure comprises selecting a predetermined number of the sets of SQC metrics from the k-d tree data structure and respective associated reference coverage data sets.

16. The method of claim 15, wherein the predetermined number of the sets of SQC metrics is less than a number of total reference coverage data sets thereby decreasing usage of a computational resource of one or more computing devices.

17. The method of claim 1, further comprising sequencing the nucleic acid samples from the subject.

18. The method of claim 5, wherein normalizing the sample coverage data set is performed via parallel processing.

19. An apparatus, comprising:

one or more processors; and a memory storing processor-executable instructions that, when executed by the one or more processors, cause the apparatus to:

receive, by a computing device, a sample coverage data set comprising a plurality of genomic sequences obtained from sequencing of nucleic acid samples of a subject, and sample sequencing quality control (SSQC) metrics;

group, by the computing device, sets of sequencing quality control (SQC) metrics by a k-nearest neighbor algorithm into a k-d tree data structure according to similarity, wherein each of the sets of SQC metrics is associated with a respective reference coverage data set;

select, by the computing device, a reference panel of reference coverage data sets using the k-d tree data structure, wherein the selected reference coverage data sets have SQC metrics similar to the SSQC metrics; and identify one or more copy number variants (CNVs) by comparing, by the computing device, according to a Hidden Markov Model (HMM) and an expected coverage distribution from a mixture model, the sample coverage data set to the expected coverage distribution.

20. A computer readable medium comprising processor-executable instructions adapted to cause one or more computing devices to:

receive, by a computing device, a sample coverage data set comprising a plurality of genomic sequences obtained from sequencing of nucleic acid samples of a subject, and sample sequencing quality control (SSQC) metrics;

group, by the computing device, sets of sequencing quality control (SQC) metrics by a k-nearest neighbor algorithm into a k-d tree data structure according to similarity, wherein each of the sets of SQC metrics is associated with a respective reference coverage data set;

select, by the computing device, a reference panel of reference coverage data sets using the k-d tree data structure, wherein the selected reference coverage data sets have SQC metrics similar to the SSQC metrics; and identify one or more copy number variants (CNVs) by comparing, by the computing device, according to a Hidden Markov Model (HMM) and an expected coverage distribution from a mixture model, the sample coverage data set to the expected coverage distribution.

* * * * *